US008826474B2

(12) United States Patent
Jackson

(10) Patent No.: US 8,826,474 B2
(45) Date of Patent: *Sep. 9, 2014

(54) MODULAR MULTI-ARTICULATED PATIENT SUPPORT SYSTEM

(71) Applicant: Roger P. Jackson, Prairie Village, KS (US)

(72) Inventor: Roger P. Jackson, Prairie Village, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/902,525

(22) Filed: May 24, 2013

(65) Prior Publication Data
US 2013/0254993 A1    Oct. 3, 2013

Related U.S. Application Data

(63) Continuation of application No. 13/317,012, filed on Oct. 6, 2011, now Pat. No. 8,719,979, which is a (Continued)

(51) Int. Cl.
| | |
|---|---|
| A61G 13/02 | (2006.01) |
| A61G 13/04 | (2006.01) |
| A61B 6/04 | (2006.01) |
| A61G 7/00 | (2006.01) |
| A61G 13/00 | (2006.01) |
| A61G 13/08 | (2006.01) |
| A61G 13/06 | (2006.01) |
| A61G 7/008 | (2006.01) |

(52) U.S. Cl.
CPC ............. *A61G 13/02* (2013.01); *A61B 6/0407* (2013.01); *A61G 7/001* (2013.01); *A61G 13/0036* (2013.01); *A61G 2013/0054* (2013.01); *A61G 13/08* (2013.01); *A61G 13/06* (2013.01); *A61G 7/008* (2013.01); *A61G 13/04* (2013.01)
USPC .................................................. 5/611; 5/610

(58) Field of Classification Search
USPC .............. 5/607, 608, 610, 611, 613, 617, 618
See application file for complete search history.

(56) References Cited

U.S. PATENT DOCUMENTS

| 1,171,713 A | 2/1916 | Gilkerson |
|---|---|---|
| 1,667,982 A | 5/1928 | Pearson |

(Continued)

FOREIGN PATENT DOCUMENTS

| GB | 569758 | 6/1945 |
|---|---|---|
| GB | 810956 | 3/1959 |

(Continued)

OTHER PUBLICATIONS

Complaint for Patent Infringement, *Jackson v. Mizuho Orthopedic Sys., Inc.*, No. 4:12-CV-01031 (W.D. Mo. Aug. 7, 2012).

(Continued)

*Primary Examiner* — Michael Trettel
(74) *Attorney, Agent, or Firm* — Polsinelli PC

(57) ABSTRACT

A modular, multi-articulated patient support system includes independently adjustable columns connected by an adjustable base and supporting a patient support structure. Each column includes rotation, angulation and separation adjustment structure. The patient support may be raised, lowered and rotated about a longitudinal axis in either horizontal or tilted orientation. The patient support includes a body support rotatably coupled with right and left leg supports disengageable at the outboard ends, that can be tilted, rotated and locked in place. An intermediate brace engages the base when the outboard ends of the leg supports are disengaged. The patient support structure may include two pairs of patient supports, each attached at the outboard end of a column and having a free inboard end. A coordinated drive system raises, lowers, tilts and rotates the patient supports, which may be positioned in overlapping relation. The pairs of patient supports may be rotated in unison to achieve 180° repositioning of a patient.

24 Claims, 22 Drawing Sheets

Related U.S. Application Data continuation of application No. 12/460,702, filed on Jul. 23, 2009, now Pat. No. 8,060,960, which is a continuation of application No. 11/788,513, filed on Apr. 20, 2007, now Pat. No. 7,565,708, and a continuation-in-part of application No. 11/159,494, filed on Jun. 23, 2005, now Pat. No. 7,343,635, which is a continuation-in-part of application No. 11/062,775, filed on Feb. 22, 2005, now Pat. No. 7,152,261.

(60) Provisional application No. 60/798,288, filed on May 5, 2006.

(56) References Cited

U.S. PATENT DOCUMENTS

| | | |
|---|---|---|
| 1,799,692 A | 4/1931 | Knott |
| 1,938,006 A | 12/1933 | Blanchard |
| 2,261,297 A | 11/1941 | Seib |
| 2,475,003 A | 7/1949 | Black |
| 2,636,793 A * | 4/1953 | Meyer ................. 5/618 |
| 3,046,071 A | 7/1962 | Shampaine et al. |
| 3,281,141 A | 10/1966 | Smiley et al. |
| 3,584,321 A | 6/1971 | Buchanan |
| 3,599,964 A | 8/1971 | Magni |
| 3,766,384 A | 10/1973 | Anderson |
| 3,814,414 A | 6/1974 | Chapa |
| 3,832,742 A | 9/1974 | Stryker |
| 4,101,120 A | 7/1978 | Seshima |
| 4,131,802 A | 12/1978 | Braden et al. |
| 4,144,880 A | 3/1979 | Daniels |
| 4,148,472 A | 4/1979 | Rais et al. |
| 4,175,550 A | 11/1979 | Leininger et al. |
| 4,186,917 A | 2/1980 | Rais et al. |
| 4,227,269 A | 10/1980 | Johnston |
| 4,230,100 A | 10/1980 | Moon |
| 4,474,364 A | 10/1984 | Brendgord |
| 4,503,844 A | 3/1985 | Siczek |
| 4,552,346 A | 11/1985 | Schnelle et al. |
| 4,712,781 A | 12/1987 | Watanabe |
| 4,718,077 A | 1/1988 | Moore et al. |
| 4,763,643 A | 8/1988 | Vrzalik |
| 4,872,657 A | 10/1989 | Lussi |
| 4,937,901 A | 7/1990 | Brennan |
| 4,970,737 A | 11/1990 | Sagel |
| 5,088,706 A | 2/1992 | Jackson |
| 5,131,106 A * | 7/1992 | Jackson ................. 5/613 |
| 5,208,928 A | 5/1993 | Kuck et al. |
| 5,210,888 A | 5/1993 | Canfield |
| 5,231,741 A | 8/1993 | Maguire |
| 5,239,716 A | 8/1993 | Fisk |
| 5,393,018 A | 2/1995 | Roth et al. |
| 5,444,882 A | 8/1995 | Andrews et al. |
| 5,461,740 A * | 10/1995 | Pearson ................. 5/611 |
| 5,468,216 A | 11/1995 | Johnson et al. |
| 5,579,550 A | 12/1996 | Bathrick et al. |
| 5,588,705 A | 12/1996 | Chang |
| 5,613,254 A | 3/1997 | Clayman et al. |
| 5,640,730 A | 6/1997 | Godette |
| 5,658,315 A | 8/1997 | Lamb et al. |
| 5,659,909 A | 8/1997 | Pfeuffer et al. |
| 5,774,914 A | 7/1998 | Johnson et al. |
| 5,794,286 A | 8/1998 | Scott et al. |
| 5,862,549 A | 1/1999 | Morton et al. |
| 5,870,784 A | 2/1999 | Elliott |
| 6,000,076 A | 12/1999 | Webster et al. |
| 6,260,220 B1 * | 7/2001 | Lamb et al. ................. 5/607 |
| 6,286,164 B1 | 9/2001 | Lamb et al. |
| 6,295,671 B1 | 10/2001 | Reesby et al. |
| 6,438,777 B1 | 8/2002 | Bender |
| 6,499,162 B1 | 12/2002 | Lu |
| 6,505,365 B1 * | 1/2003 | Hanson et al. ................. 5/613 |
| 6,526,610 B1 | 3/2003 | Hand et al. |
| 6,634,043 B2 | 10/2003 | Lamb et al. |
| 6,638,299 B2 | 10/2003 | Cox |
| 6,681,423 B2 | 1/2004 | Zachrisson |
| 6,701,553 B1 | 3/2004 | Hand et al. |
| 6,971,131 B2 | 12/2005 | Bannister |
| 6,971,997 B1 | 12/2005 | Ryan et al. |
| 7,003,828 B2 | 2/2006 | Roussy |
| 7,055,195 B2 | 6/2006 | Roussy |
| 7,089,612 B2 | 8/2006 | Rocher et al. |
| 7,103,931 B2 | 9/2006 | Somasundaram et al. |
| 7,137,160 B2 | 11/2006 | Hand et al. |
| 7,152,261 B2 * | 12/2006 | Jackson ................. 5/600 |
| 7,171,709 B2 | 2/2007 | Weismiller |
| 7,234,180 B2 * | 6/2007 | Horton et al. ................. 5/613 |
| 7,331,557 B2 | 2/2008 | Dewert |
| 7,343,635 B2 * | 3/2008 | Jackson ................. 5/611 |
| 7,565,708 B2 | 7/2009 | Jackson |
| 7,596,820 B2 | 10/2009 | Nielsen et al. |
| 7,739,762 B2 | 6/2010 | Lamb et al. |
| 8,060,960 B2 | 11/2011 | Jackson |
| 2001/0037524 A1 | 11/2001 | Truwit |
| 2004/0098804 A1 | 5/2004 | Varadharajulu et al. |
| 2004/0133983 A1 * | 7/2004 | Newkirk et al. ................. 5/624 |
| 2006/0123546 A1 | 6/2006 | Horton et al. |
| 2006/0185090 A1 | 8/2006 | Jackson |
| 2007/0107126 A1 | 5/2007 | Koch et al. |
| 2007/0192960 A1 | 8/2007 | Jackson |
| 2008/0000028 A1 * | 1/2008 | Lemire et al. ................. 5/618 |
| 2008/0127419 A1 | 6/2008 | Jensen |
| 2011/0099716 A1 | 5/2011 | Jackson |
| 2011/0107516 A1 | 5/2011 | Jackson |
| 2011/0107517 A1 | 5/2011 | Lamb et al. |
| 2012/0023672 A1 | 2/2012 | Jackson |
| 2012/0246829 A1 | 10/2012 | Lamb et al. |
| 2012/0255122 A1 | 10/2012 | Diel et al. |
| 2013/0254992 A1 | 10/2013 | Jackson |
| 2013/0254993 A1 * | 10/2013 | Jackson ................. 5/607 |
| 2013/0254994 A1 * | 10/2013 | Jackson ................. 5/607 |
| 2013/0254995 A1 | 10/2013 | Jackson |
| 2013/0254996 A1 | 10/2013 | Jackson |
| 2013/0254997 A1 | 10/2013 | Jackson |
| 2013/0318718 A1 | 12/2013 | Jackson |
| 2013/0318719 A1 | 12/2013 | Jackson |
| 2013/0326812 A1 | 12/2013 | Jackson |
| 2013/0326813 A1 | 12/2013 | Jackson |

FOREIGN PATENT DOCUMENTS

| | | |
|---|---|---|
| JP | S53763 | 1/1978 |
| JP | 2000-060995 | 2/2000 |
| WO | WO99/07320 | 2/1999 |
| WO | WO00/62731 | 10/2000 |
| WO | WO01/60308 | 8/2001 |
| WO | WO03/070145 | 8/2003 |
| WO | WO2009/054969 | 4/2009 |
| WO | WO2009/100692 | 8/2009 |

OTHER PUBLICATIONS

First Amended Complaint for Patent Infringement and Correction of Inventorship, *Jackson* v. *Mizuho Orthopedic Sys., Inc.*, No. 4:12-CV-01031 (W.D. Mo. Sep. 21, 2012).

Defendant Mizuho Orthopedic Systems, Inc.'s Answer to First Amended Complaint and Counterclaims, *Jackson* v. *Mizuho Orthopedic Sys., Inc.*, No. 4:12-CV-01031 (W.D. Mo. Nov. 1, 2012).

Plaintiff Roger P. Jackson, MD's, Reply to Counterclaims, *Jackson* v. *Mizuho Orthopedic Sys., Inc.*, No. 4:12-CV-01031 (W.D. Mo. Nov. 26, 2012).

Roger P. Jackson's Disclosure of Asserted Claims and Preliminary Infringement Contentions, *Jackson* v. *Mizuho Orthopedic Sys., Inc.*, No. 4:12-CV-01031 (W.D. Mo. Jan. 4, 2013).

Second Amended Complaint for Patent Infringement, for Correction of Inventorship, for Breach of a Non-Disclosure and Confidentiality Agreement, and for Misappropriation of Dr. Jackson's Right of Publicity, *Jackson* v. *Mizuho Orthopedic Sys., Inc.*, No. 4:12-CV-01031 (W.D. Mo. Jan. 28, 2013).

Defendant Mizuho Orthopedic Systems, Inc.'s Answer to Second Amended Complaint and Counterclaims, *Jackson* v. *Mizuho Orthopedic Sys., Inc.*, No. 4:12-CV-01031 (W.D. Mo. Feb. 19, 2013).

(56) References Cited

OTHER PUBLICATIONS

Defendant Mizuho Osi's Invalidity Contentions Pursuant to the Parties' Joint Scheduling Order, *Jackson* v. *Mizuho Orthopedic Sys., Inc.*, No. 4:12-CV-01031 (W.D. Mo. Feb. 22, 2013).
Plaintiff Roger P. Jackson, MD's, Reply to Second Counterclaims, *Jackson* v. *Mizuho Orthopedic Sys., Inc.*, No. 4:12-CV-01031 (W.D. Mo. Mar. 12, 2013).
Roger P. Jackson, MD's Disclosure of Proposed Terms to Be Construed, *Jackson* v. *Mizuho Orthopedic Sys., Inc.*, No. 4:12-CV-01031 (W.D. Mo. Apr. 5, 2013).
Defendant Mizuho Orthopedic Systems, Inc.'s Disclosure of Proposed Terms and Claim Elements for Construction, *Jackson* v. *Mizuho Orthopedic Sys., Inc.*, No. 4:12-CV-01031 (W.D. Mo. Apr. 5, 2013).
Mizuho Orthopedic Systems, Inc.'s Disclosure of Proposed Claim Constructions and Extrinsic Evidence, *Jackson* v. *Mizuho Orthopedic Sys., Inc.*, No. 4:12-CV-01031 (W.D. Mo. May 13, 2013).
Plaintiff Roger P. Jackson, MD's Disclosure of Preliminary Proposed Claim Constructions, *Jackson* v. *Mizuho Orthopedic Sys., Inc.*, No. 4:12-CV-01031 (W.D. Mo. May 13, 2013).
Defendant Mizuho Osi's Amended Invalidity Contentions Pursuant to the Parties' Joint Scheduling Order, *Jackson* v. *Mizuho Orthopedic Sys., Inc.*, No. 4:12-CV-01031 (W.D. Mo. May 15, 2013).
Joint Claim Construction Chart and Joint Prehearing Statement, *Jackson* v. *Mizuho Orthopedic Sys., Inc.*, No. 4:12-CV-01031 (W.D. Mo. Jun. 7, 2013).
Defendant Mizuho Orthopedic Systems, Inc.'s Objections and Responses to Plaintiff's First Set of Interrogatories, *Jackson* v. *Mizuho Orthopedic Sys., Inc.*, No. 4:12-CV-01031 (W.D. Mo. Jun. 24, 2013).
Defendant Mizuho Orthopedic Systems, Inc.'s Opening Claim Construction Brief, *Jackson* v. *Mizuho Orthopedic Sys., Inc.*, No. 4:12-CV-01031 (W.D. Mo. Jul. 31, 2013).
Plaintiff Roger P. Jackson, MD's Opening Claim Construction Brief, *Jackson* v. *Mizuho Orthopedic Sys., Inc.*, No. 4:12-CV-01031 (W.D. Mo. Jul. 31, 2013).
Appendix A Amended Infringement Contentions Claim Chart for Mizuho's Axis System Compared to U.S. Patent No. 7,565,708, *Jackson* v. *Mizuho Orthopedic Sys., Inc.*, No. 4:12-CV-01031 (W.D. Mo. Aug. 12, 2013).
Appendix B Amended Infringement Contentions Claim Chart for Mizuho's Axis System Compared to U.S. Patent No. 8,060,960, *Jackson* v. *Mizuho Orthopedic Sys., Inc.*, No. 4:12-CV-01031 (W.D. Mo. Aug. 12, 2013).
Appendix C Amended Infringement Contentions Claim Chart for Mizuho's Proaxis System Compared to U.S. Patent No. 7,565,708, *Jackson* v. *Mizuho Orthopedic Sys., Inc.*, No. 4:12-CV-01031 (W.D. Mo. Aug. 12, 2013).
Appendix D Amended Infringement Contentions Claim Chart for Mizuho's Proaxis System Compared to U.S. Patent No. 8,060,960, *Jackson* v. *Mizuho Orthopedic Sys., Inc.*, No. 4:12-CV-01031 (W.D. Mo. Aug. 12, 2013).
Plaintiff Roger P. Jackson, MD's Responsive Claim Construction Brief, *Jackson* v. *Mizuho Orthopedic Sys., Inc.*, No. 4:12-CV-01031 (W.D. Mo. Aug. 16, 2013).
Defendant Mizuho Orthopedic Systems, Inc's Brief in Response to Plaintiff's Opening Claim Construction Brief, *Jackson* v. *Mizuho Orthopedic Sys., Inc.*, No. 4:12-CV-01031 (W.D. Mo. Aug. 16, 2013).
Plaintiff Roger P. Jackson, Md's Suggestions in Support of His Motion to Strike Exhibit A of Mizuho's Opening Claim Construction Brief, *Jackson* v. *Mizuho Orthopedic Sys., Inc.*, No. 4:12-CV-01031 (W.D. Mo. Aug. 16, 2013).
Defendant Mizuho Orthopedic Systems, Inc.'s Opposition to Plaintiff's Motion to Strike, *Jackson* v. *Mizuho Orthopedic Sys., Inc.*, No. 4:12-CV-01031 (W.D. Mo. Sep. 3, 2013).
Transcript of Claim Construction Hearing, *Jackson* v. *Mizuho Orthopedic Sys., Inc.*, No. 4:12-CV-01031 (W.D. Mo. Oct. 11, 2013).
Plaintiff Roger P. Jackson, MD's Claim Construction Presentation for U.S. District Judge Nanette K. Laughrey, *Jackson* v. *Mizuho Orthopedic Sys., Inc.*, No. 4:12-CV-01031 (W.D. Mo. Oct. 11, 2013).
Mizuho's Claim Construction Argument, *Jackson* v. *Mizuho Orthopedic Sys., Inc.*, No. 4:12-CV-01031 (W.D. Mo. Oct. 11, 2013).
Order, *Jackson* v. *Mizuho Orthopedic Sys., Inc.*, No. 4:12-CV-01031 (W.D. Mo. Apr. 4, 2014).
Brochure of OSI on Modular Table System 90D, pp. 1-15, date of first publication: Unknown.
Brochure of Smith & Nephew on Spinal Positioning System, 2003, 2004.
Pages from website http://www.schaerermayfieldusa.com, pp. 1-5, date of first publication: Unknown.

\* cited by examiner

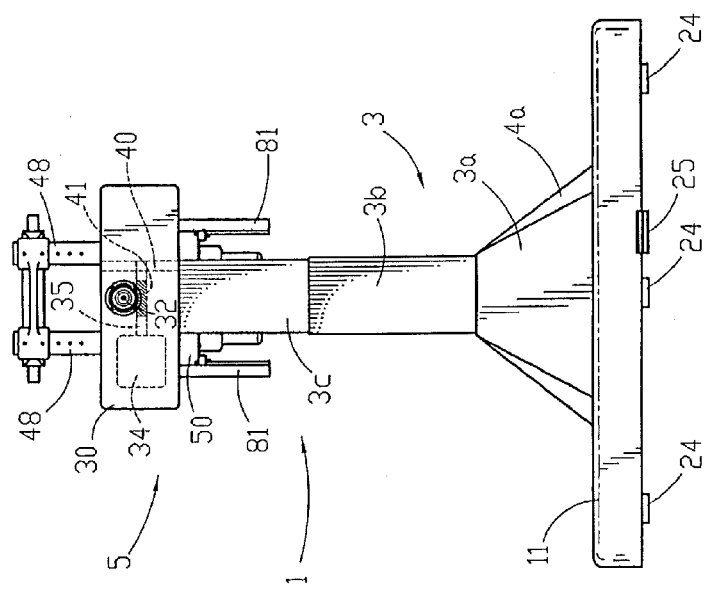

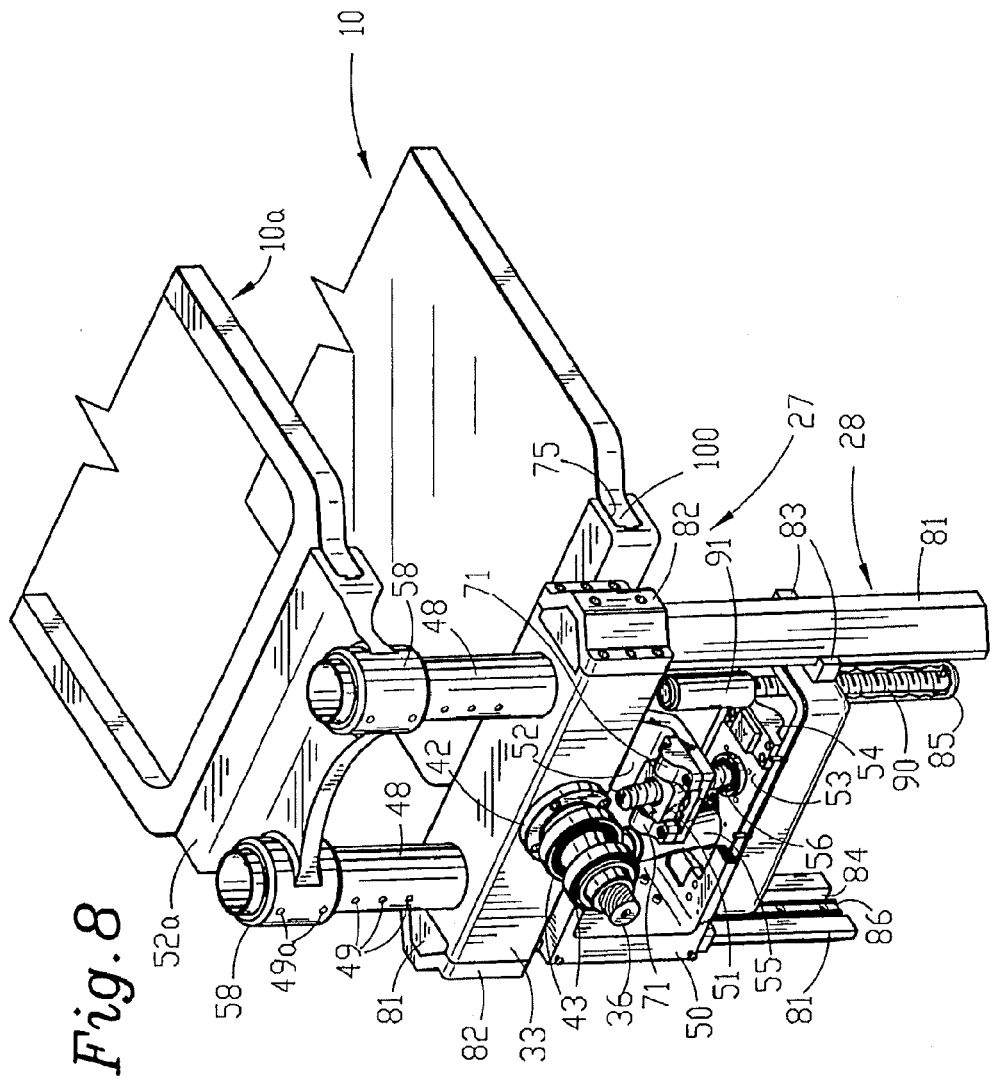

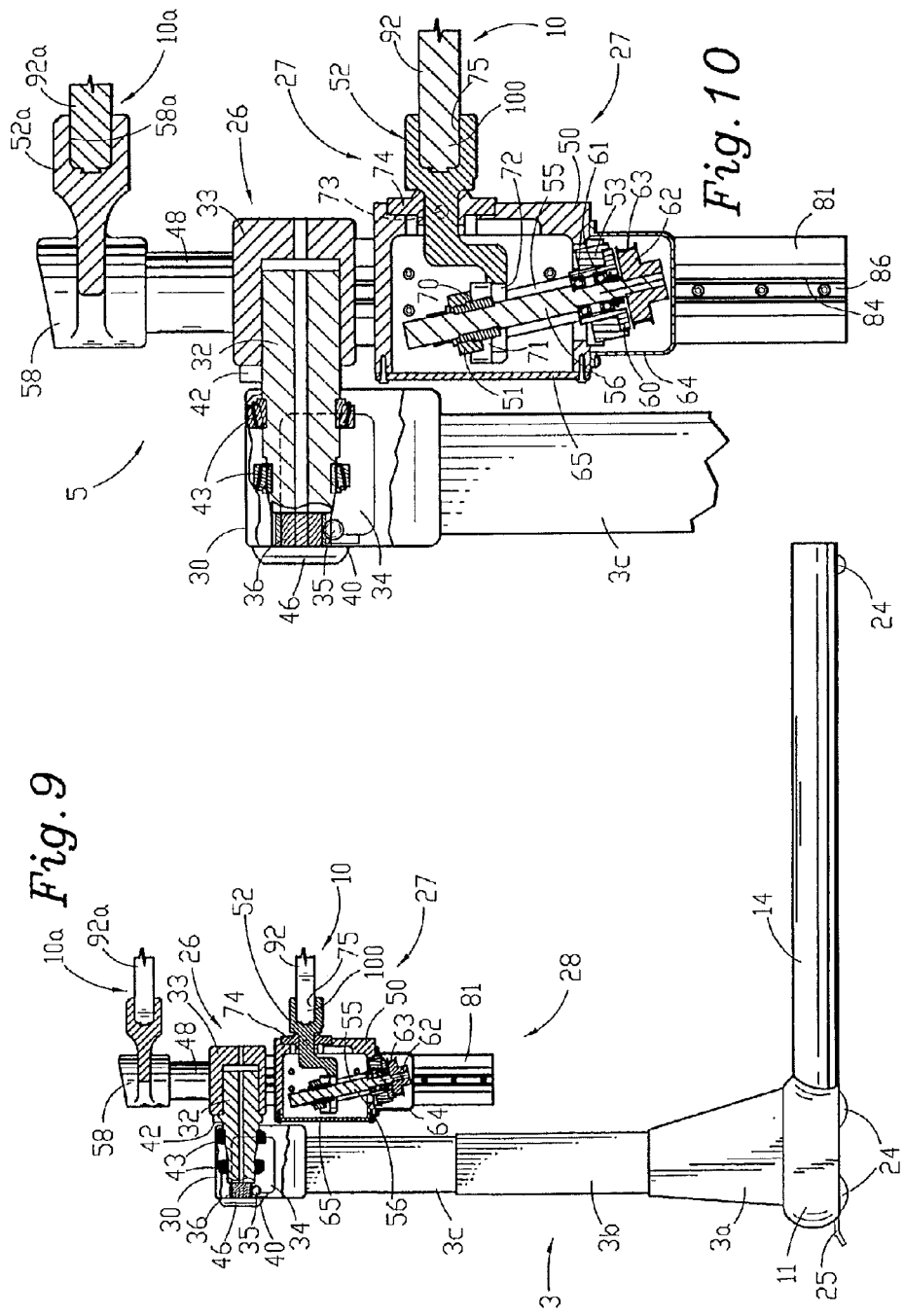

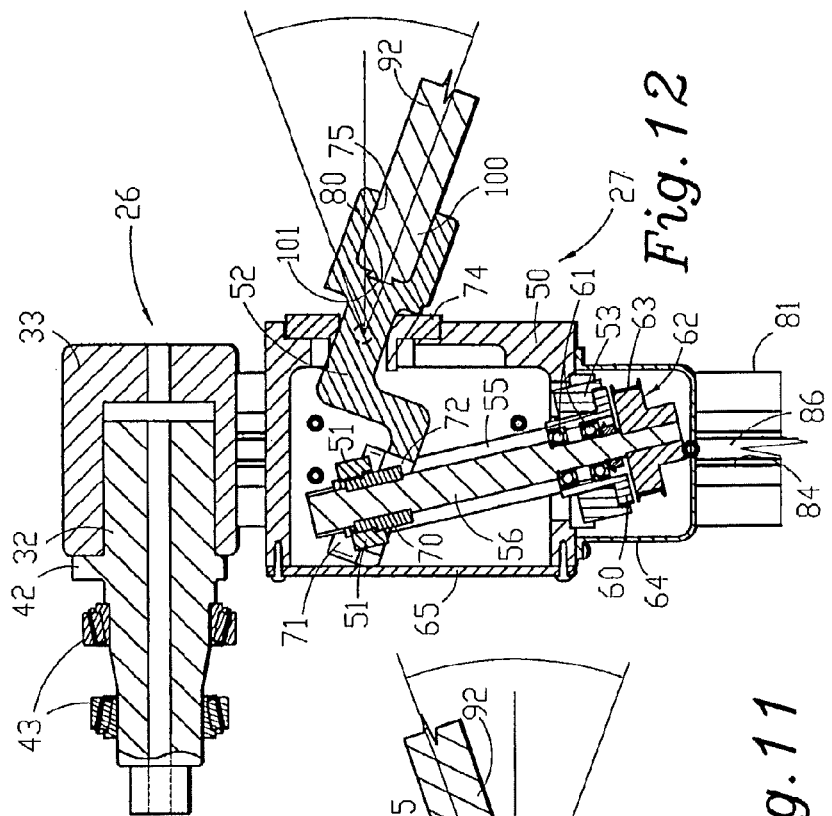
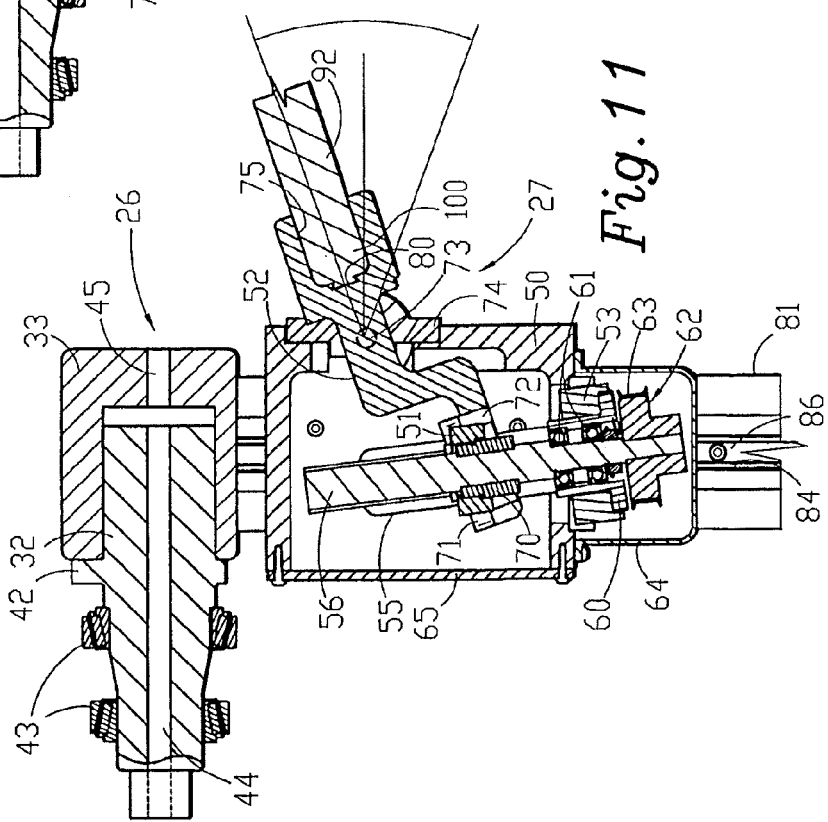

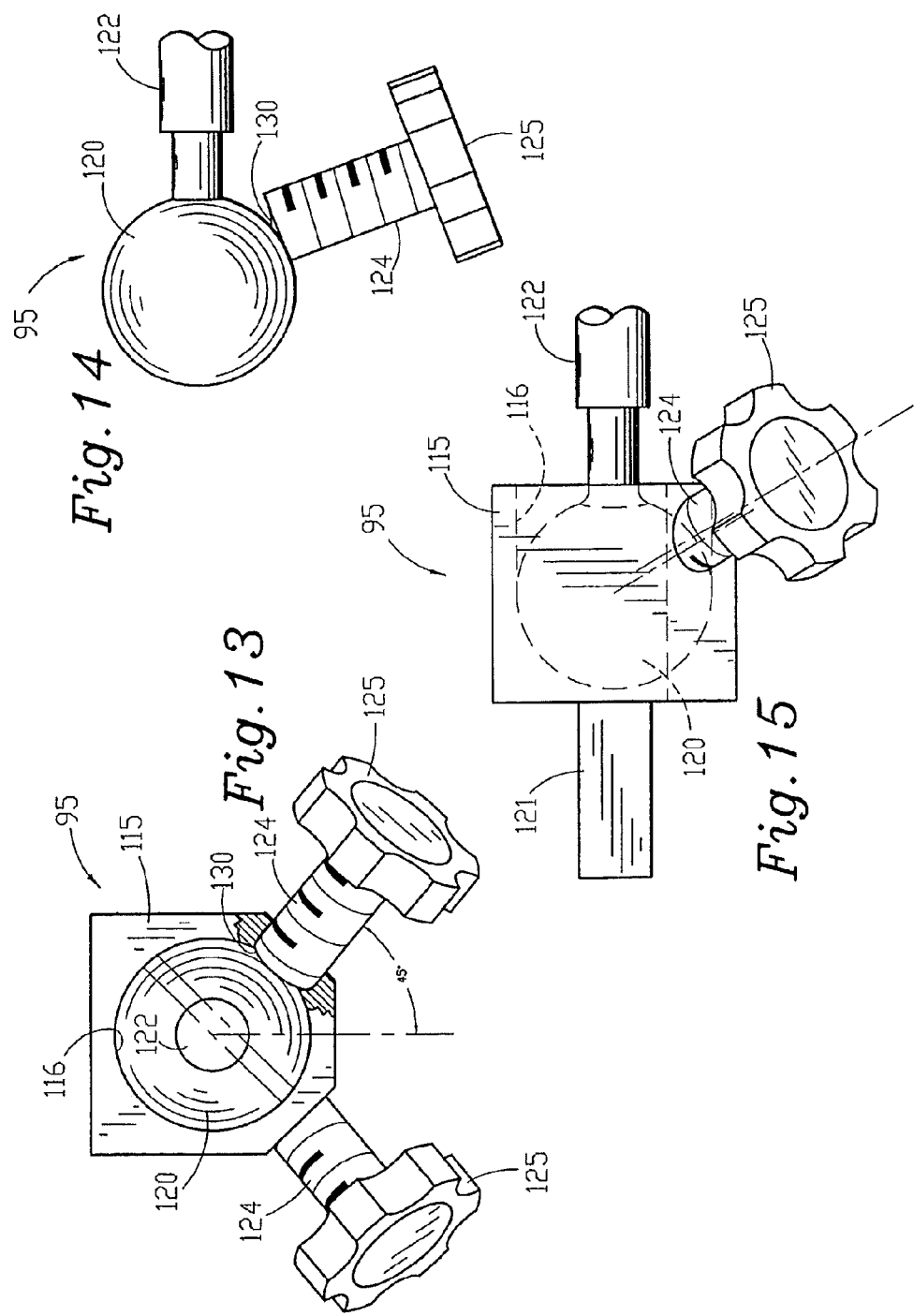

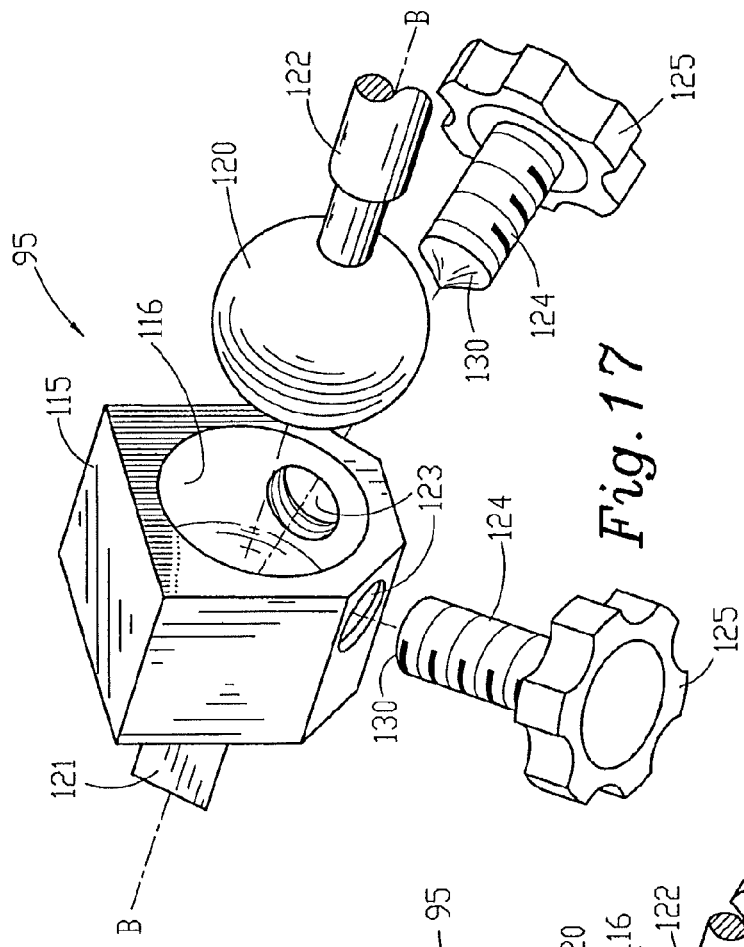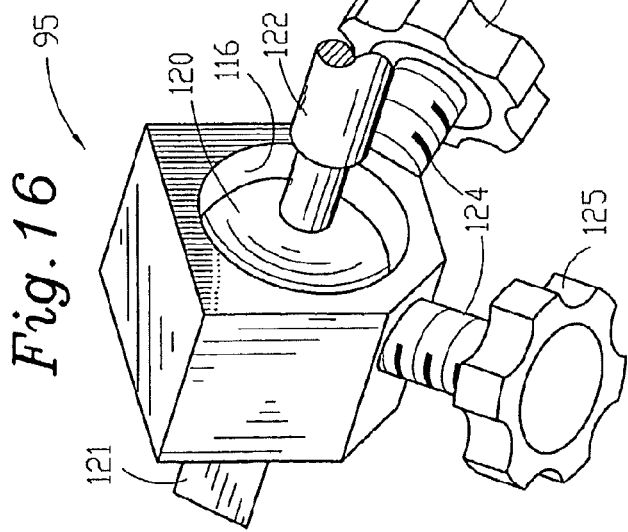

MODULAR MULTI-ARTICULATED PATIENT SUPPORT SYSTEM

CROSS REFERENCE OF RELATED APPLICATIONS

This application is a continuation-in-part of U.S. application Ser. No. 13/317,012 filed Oct. 6, 2011, now U.S. Pat. No. 8,719,979, entitled Patient Positioning Support Structure, which application is a continuation of U.S. Ser. No. 12/460,702, filed Jul. 23, 2009, now U.S. Pat. No. 8,060,960, which is a continuation of U.S. Ser. No. 11/788,513, filed Apr. 20, 2007, now U.S. Pat. No. 7,565,708, which claims the benefit of U.S. Provisional Application No. 60/798,288 filed May 5, 2006 and is also a continuation-in-part of U.S. patent application Ser. No. 11/159,494 filed Jun. 23, 2005, now U.S. Pat. No. 7,343,635, which is a continuation-in-part of U.S. patent application Ser. No. 11/062,775 filed Feb. 22, 2005, now U.S. Pat. No. 7,152,261. The disclosures of all the preceding applications and patents are incorporated by reference herein.

FIELD OF THE INVENTION

The present invention is broadly concerned with a system for positioning and supporting a patient during examination and treatment, including medical procedures such as imaging, surgery and the like. More particularly, it is concerned with a system having patient support modules that can be independently adjusted for selective positioning of portions of the patient's body by movement up and down, tilting, pivoting, angulating or bending of the trunk in a supine, prone or lateral position, multi-axial motion of joints, rotation of the patient about an axis from a prone to a lateral to a supine position, and that is suitable for integrated computer software actuation.

BACKGROUND OF THE INVENTION

Modern surgical practice incorporates imaging techniques and technologies throughout the course of patient examination, diagnosis and treatment. For example, minimally invasive surgical techniques, such as percutaneous insertion of spinal implants, involve small incisions that are guided by continuous or repeated intraoperative imaging. These images can be processed using computer software programs that produce three dimensional images for reference by the surgeon during the course of the procedure. If the patient support surface is not radiolucent or compatible with the imaging technologies, it may be necessary to interrupt the surgery periodically in order to remove the patient to a separate surface for imaging followed by transfer back to the operating support surface for resumption of the surgical procedure. Such patient transfers for imaging purposes may be avoided by employing radiolucent and other imaging compatible systems. The patient support system should also be constructed to permit unobstructed movement of the imaging equipment and other surgical equipment around, over and under the patient throughout the course of the surgical procedure without contamination of the sterile field.

It is also necessary that the patient support system be constructed to provide optimum access to the surgical field by the surgery team. Some procedures require positioning of portions of the patient's body in different ways at different times during the procedure. Some procedures, for example, spinal surgery, involve access through more than one surgical site or field. Since all of these fields may not be in the same plane or anatomical location, the patient support surfaces should be adjustable and capable of providing support in different planes for different parts of the patient's body as well as different positions or alignments for a given part of the body. Preferably, the support surface should be adjustable to provide support in separate planes and in different alignments for the head and upper trunk portion of the patient's body, the lower trunk and pelvic portion of the body as well as each of the limbs independently.

Certain types of surgery, such as orthopedic surgery, may require that the patient or a part of the patient be repositioned during the procedure while in some cases maintaining the sterile field. Where surgery is directed toward motion preservation procedures, such as by installation of artificial joints, spinal ligaments and total disc prostheses, for example, the surgeon must be able to manipulate certain joints while supporting selected portions of the patient's body during surgery in order to facilitate the procedure. It is also desirable to be able to test the range of motion of the surgically repaired or stabilized joint and to observe the gliding movement of the reconstructed articulating prosthetic surfaces or the tension of artificial ligaments before the wound is closed. Such manipulation can be used, for example, to verify the correct positioning and function of an implanted prosthetic disc or joint replacement during a surgical procedure. Where manipulation discloses binding, suboptimal position or even crushing of the adjacent vertebrae, for example, as may occur with osteoporosis, the prosthesis can be removed and the adjacent vertebrae fused while the patient remains anesthetized. Injury which might otherwise have resulted from a "trial" use of the implant post-operatively will be avoided, along with the need for a second round of anesthesia and surgery to remove the implant or prosthesis and perform the revision, fusion or corrective surgery.

There is also a need for a patient support surface that can be rotated, articulated and angulated so that the patient can be moved from a prone to a supine position or from a prone to a 90° position and whereby intra-operative extension and flexion of at least a portion of the spinal column can be achieved. The patient support surface must also be capable of easy, selective adjustment without necessitating removal of the patient or causing substantial interruption of the procedure.

For certain types of surgical procedures, for example spinal surgeries, it may be desirable to position the patient for sequential anterior and posterior procedures. The patient support surface should also be capable of rotation about an axis in order to provide correct positioning of the patient and optimum accessibility for the surgeon as well as imaging equipment during such sequential procedures.

Orthopedic procedures may also require the use of traction equipment such as cables, tongs, pulleys and weights. The patient support system must include structure for anchoring such equipment and it must provide adequate support to withstand unequal forces generated by traction against such equipment.

Articulated robotic arms are increasingly employed to perform surgical techniques. These units are generally designed to move short distances and to perform very precise work. Reliance on the patient support structure to perform any necessary gross movement of the patient can be beneficial, especially if the movements are synchronized or coordinated. Such units require a surgical support surface capable of smoothly performing the multi-directional movements which would otherwise be performed by trained medical personnel. There is thus a need in this application as well for integration between the robotics technology and the patient positioning technology.

While conventional operating tables generally include structure that permits tilting or rotation of a patient support surface about a longitudinal axis, previous surgical support devices have attempted to address the need for access by providing a cantilevered patient support surface on one end. Such designs typically employ either a massive base to counterbalance the extended support member or a large overhead frame structure to provide support from above. The enlarged base members associated with such cantilever designs are problematic in that they may obstruct the movement of C-arm mobile fluoroscopic imaging devices. Surgical tables with overhead frame structures are bulky and may require the use of dedicated operating rooms, since in some cases they cannot be moved easily out of the way. Neither of these designs is easily portable or storable.

Thus, there remains a need for a patient support system that provides easy access for personnel and equipment, that can be easily and quickly positioned and repositioned in multiple planes without the use of massive counterbalancing support structure, and that does not require use of a dedicated operating room.

BRIEF SUMMARY OF THE INVENTION

The present invention is directed to a modular multi-articulated patient support system that permits adjustable positioning, repositioning and selectively lockable support of a patient's head and upper body, lower body and limbs in multiple individual planes while permitting tilting, rotation angulation or bending and other manipulations as well as full and free access to the patient by medical personnel and equipment. The system of the invention includes a pair of independently height-adjustable upright end support columns connected to a horizontally length-adjustable base. The support columns are coupled with respective horizontal support assemblies, which include rotation, angulation and separation adjustment structure. The horizontal support assemblies are pivotally connected to a patient support structure which may be raised, lowered and rotated about a longitudinal axis in either horizontal or tilted orientation.

The patient support structure is articulated and includes a body board rotatably coupled with a pair of leg boards. The leg boards are each disengageable at the outboard ends, and have multi-directional movement which can be locked in place. A drop down center support is shiftable to engage the base when the outboard ends of the leg boards are disengaged from the support column.

The patient support structure may also be configured to include two pairs of opposed patient supports which can be constructed as frames or boards that are, attached in spaced relation at the outboard ends to a corresponding upright end support column. A coordinated drive system raises, lowers, tilts and rotates the supports, which may be positioned in overlapping relation when the base is adjusted to a shortened, retracted position. When in an aligned position, the pairs of patient supports may be rotated in unison about a longitudinal axis to achieve 180° repositioning of a patient, from a prone to a supine position.

Various objects and advantages of this invention will become apparent from the following description taken in relation to the accompanying drawings wherein are set forth, by way of illustration and example, certain embodiments of this invention.

The drawings constitute a part of this specification, include exemplary embodiments of the present invention, and illustrate various objects and features thereof.

BRIEF DESCRIPTION OF THE DRAWINGS

FIG. 7 is a perspective end view of the system with an optional upper patient support structure installed and with the motor and drive shaft shown in phantom.

FIG. 8 is an enlarged detail of the rotation and angulation subassemblies, with parts of the housing omitted to show details of the gears.

FIG. 9 is a side elevational view of one end of the system, with parts of the rotation and angulation subassemblies shown in section.

FIG. 10 is a greatly enlarged detail of the structures shown in FIG. 9.

FIG. 11 is a greatly enlarged detail similar to that shown in FIG. 10, with the patient support structure angled upwardly.

FIG. 12 is a greatly enlarged detail similar to that shown in FIG. 10, with the patient support structure angled downwardly.

FIG. 13 is a view of a ball joint housing as viewed from the foot end, and showing a pair of set screws, with a portion of the housing broken away to show engagement of a set screw with the ball.

FIG. 14 is an exemplary perspective view of a ball joint engaged by one of the set screws.

FIG. 15 is an enlarged side perspective detail view of the ball and socket assembly shown in FIGS. 1 and 3, with the ball shown in phantom.

FIG. 16 is an enlarged perspective detail view of the ball and socket assembly depicted in FIGS. 1 and 3.

FIG. 17 is an exploded perspective view of the ball and socket assembly shown in FIG. 16.

DETAILED DESCRIPTION

Figure 1:
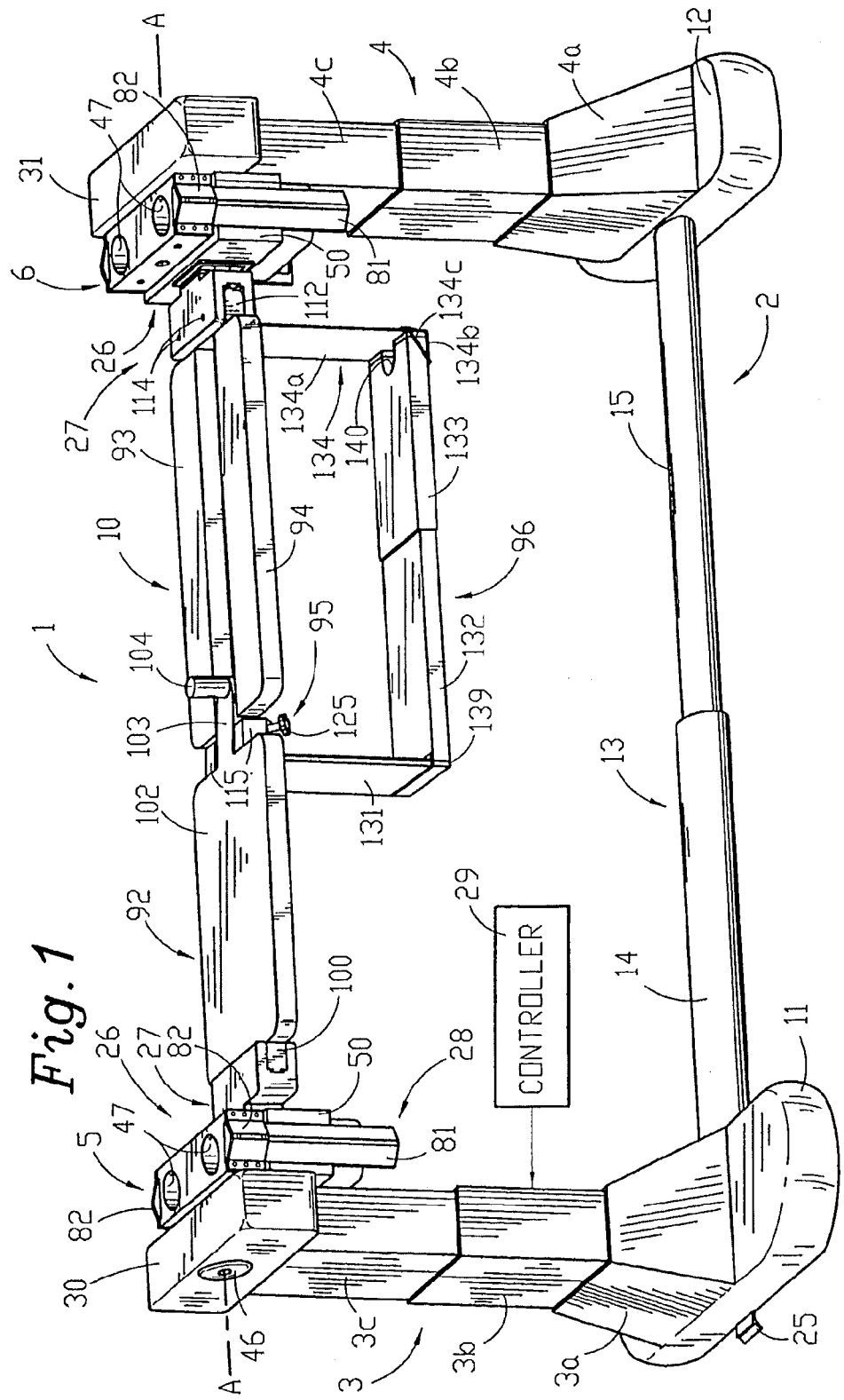
FIG. 1 is a side perspective view of a modular multi-articulated patient support system in accordance with the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring now to the drawings, a modular patient support system in accordance with the invention is generally designated by the reference numeral 1 and is depicted in FIGS. 1-17. The system 1 broadly includes an elongate length-adjustable base 2 surmounted at either end by respective first and second upright support piers or columns 3 and 4 which are connected to respective first and second horizontal support assemblies 5 and 6. Between them, the support assemblies 5 and 6 uphold an elongated patient support structure 10 and optionally, a removable second patient support structure 10a (FIG. 8).

When viewed from above, the base 2, has an approximately I-shaped configuration, including first and second low stabilizing plinths or feet 11 and 12 adjustably interconnected by a base rail or crossbar 13. The crossbar 13 includes an expansion mechanism of first and second telescoping rail sections 14 and 15. The first rail section 14 is substantially hollow and sized for reception of the retracting second rail section 15. The crossbar 13 may be selectively elongated and shortened as needed when a portion of the length of the second rail 15 is slidingly and telescopically received within the first rail 14. The crossbar 13 also includes a locking assembly 20 (FIG. 3), which may include a releasable rack 21 positioned on the inner surface of the first rail 14, and a pinion gear 22 coupled with the end of the second rail 15, or any other suitable structure enabling extension, retraction and selective locking of the crossbar 13. The horizontal telescoping action of the crossbar 13 and engagement/disengagement of the locking assembly 20 may be actuated by a motor 23 housed within the foot 11 or 12.

Figure 3:
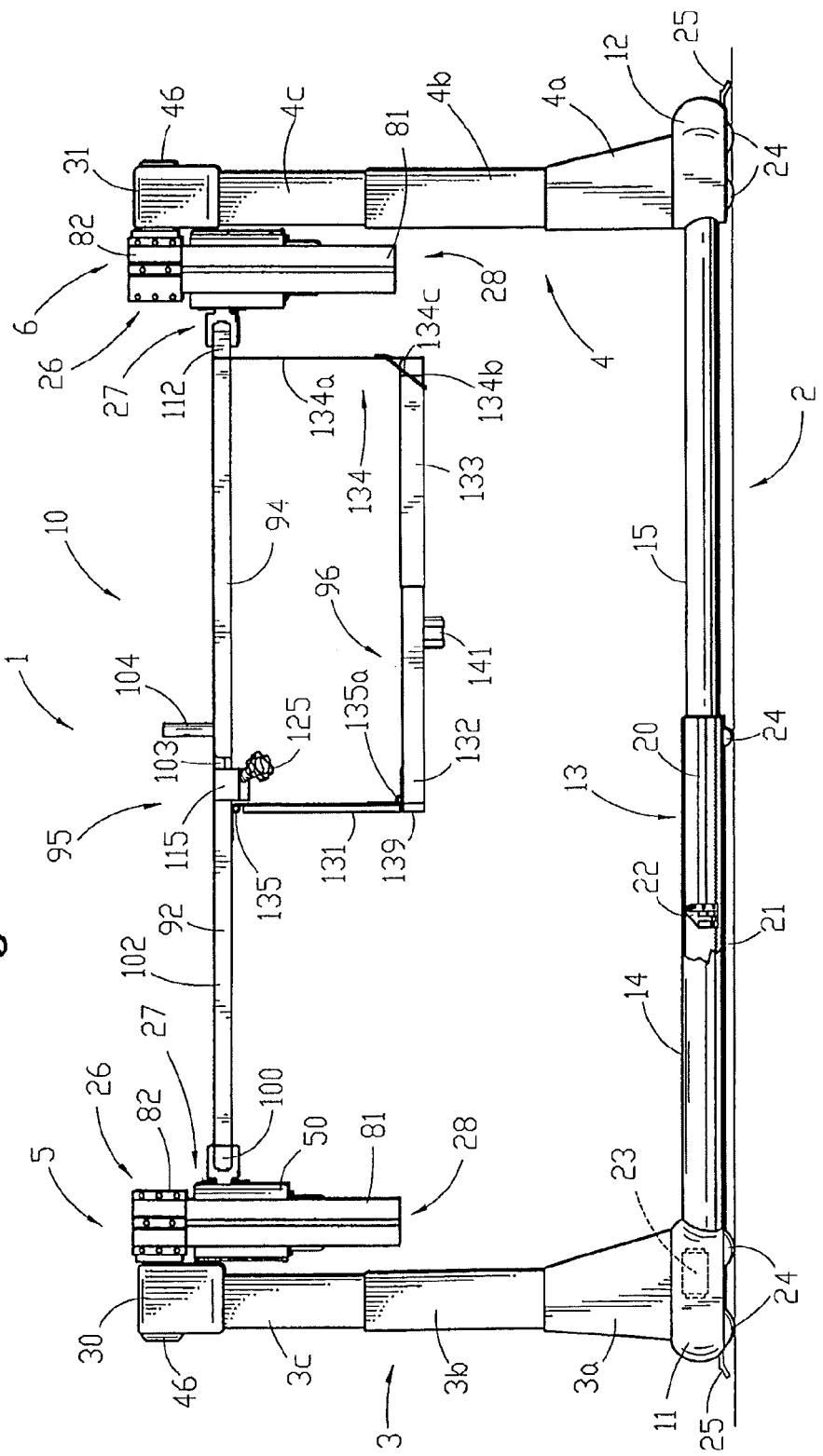
FIG. 3 is a side elevational view of the system.
Figure 4:
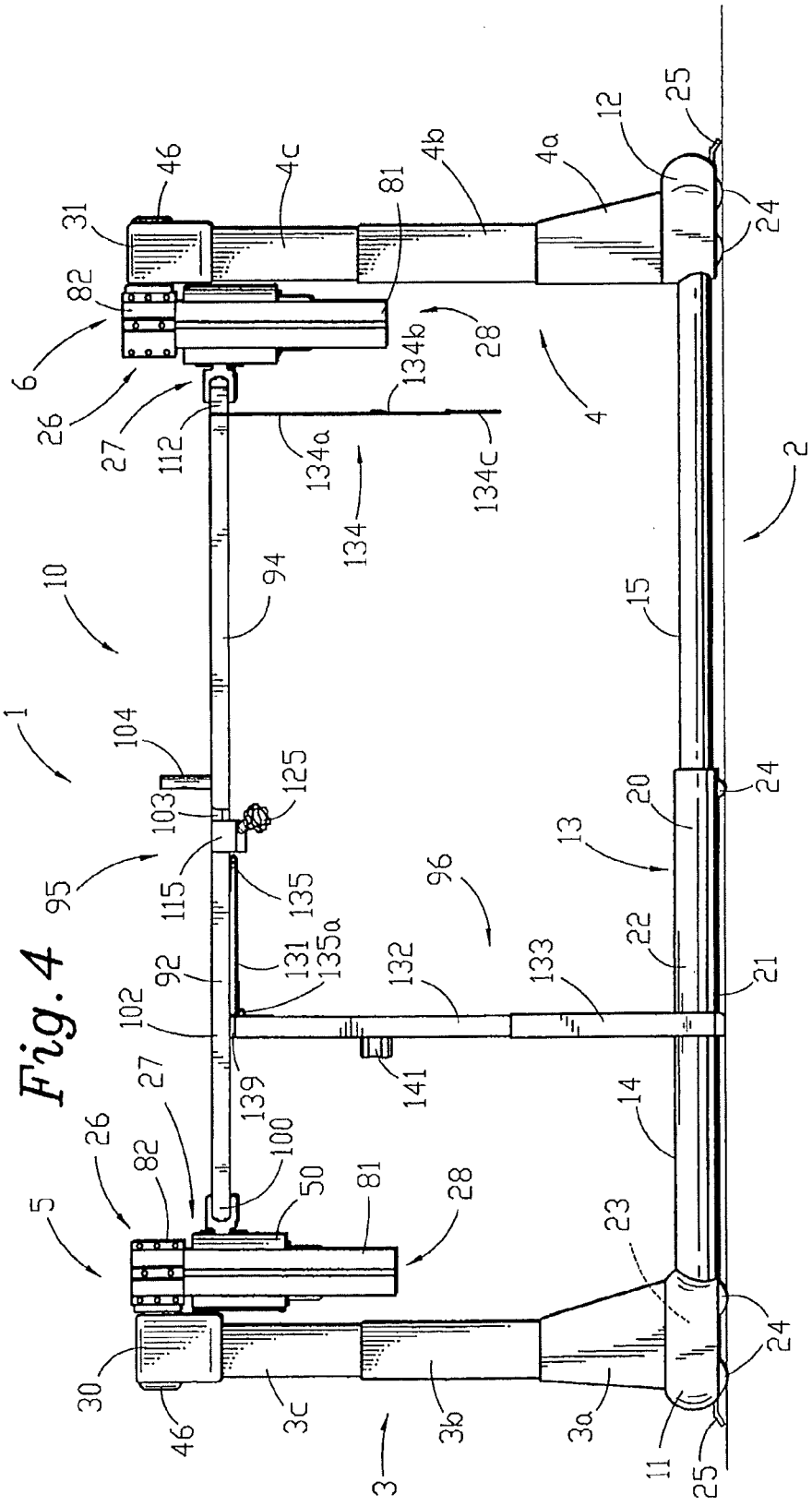
FIG. 4 is a side elevational view similar to that shown in FIG. 3, with the pillow support structure disengaged from the bracket and pivoted 90° to form an upright brace.

As best shown in FIGS. 3 and 4, the system is optionally equipped with a carriage assembly consisting of a series of spaced apart casters or wheels 24 extending below the feet 11 and 12 and center portion of the first rail 14. The wheels 24 associated with the feet 11 and 12 are each equipped with a floorlock foot lever 25 that operates to disengage the wheels and lower the foot 11 or 12 into a floor-engaging position. In this lowered position the combined weight of the base 2 and respective upright support column 3 or 4 serves as a brake against inadvertent shifting of the system 2.

The first and second feet 11 and 12 are surmounted by respective first and second upright end supports or columns 3 and 4. These columns each include a plurality of telescoping lift arm segments 3a, 3b and 3c or 4a, 4b and 4c which permit the height of each of the columns 3 and 4 to be selectively increased and decreased in order to raise and lower the attached patient support structure 10. It is foreseen that the base 2 and vertical supports 3 and 4 may be constructed so that the first foot 11 and support column 3 have substantially greater mass than the second foot 12 and support column 4 or vice versa in order to accommodate the uneven weight distribution of the human body. Such reduction in size at the foot end of the system 1 may be employed in some embodiments to facilitate the approach of personnel and equipment, for example, when a patient is positioned in a lithotomy position.

Each of the horizontal support assemblies 5 and 6 includes a rotation subassembly 26 and angulation subassembly 27 which are interconnected by a separation subassembly 28 and associated circuitry linked to a controller 29 (FIG. 1) for cooperative and integrated actuation and operation. The rotational subassembly 26 enables coordinated rotation of the patient support structure 10 about a longitudinal axis. The angulation subassembly 27 enables independent angular adjustment of each end of the patient support structure 10 and selective tilting of the longitudinal axis. The separation subassembly 28 enables each end of the patient support structure 10 to be raised and lowered with respect to an optional second patient support structure 10a mounted in spaced relation to the rotation subassembly.

The rotation subassembly or mechanism 26 is shown in FIGS. 2 and 7-10 to include first and second motor housings 30 and 31 surmounting respective support columns 3 and 4. A main rotational shaft 32 extends from each motor housing 30 and 31 and turns one of a pair of corresponding rotatable blocks 33, each of which is connected to an angulation subassembly 27 by means of a separation subassembly 28.

Figure 2:
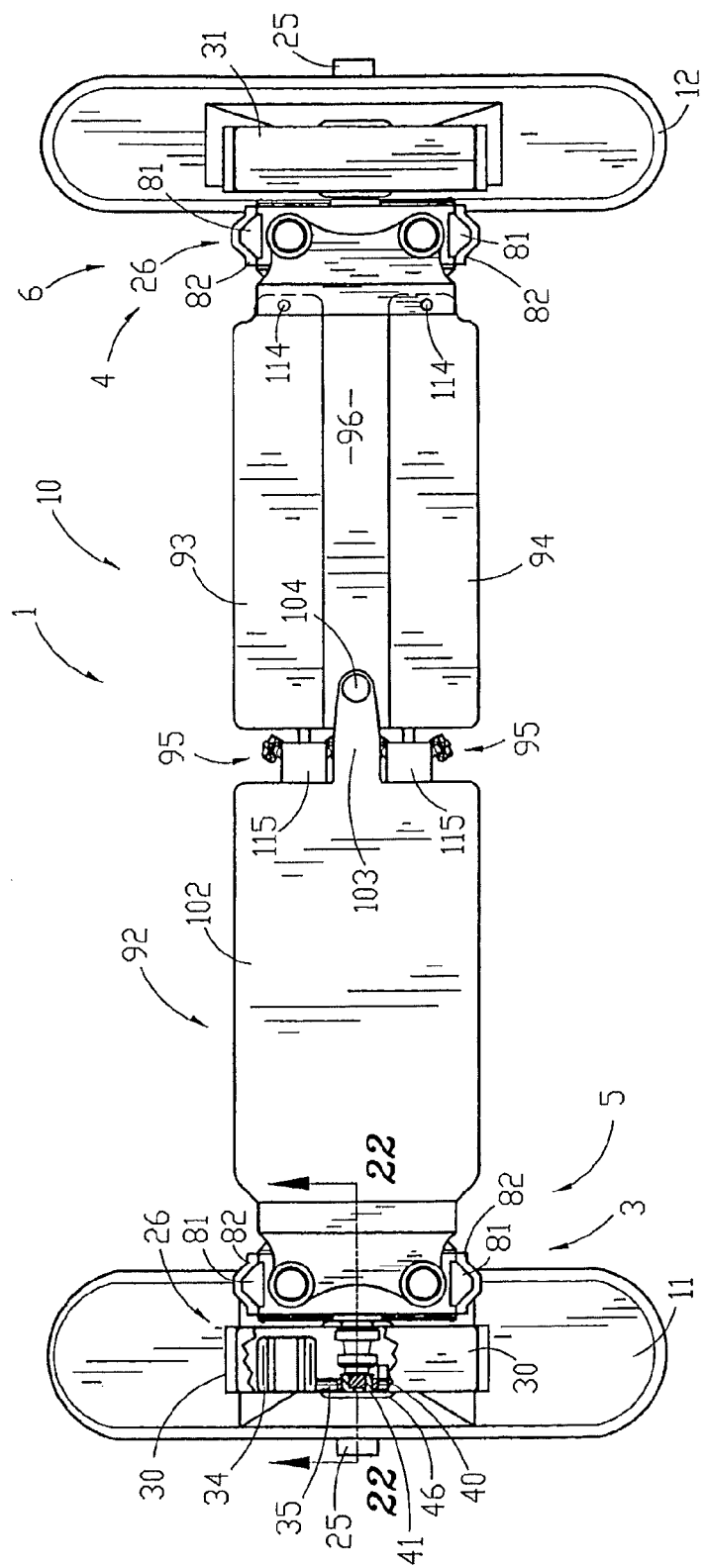
FIG. 2 is a top plan view of the system with parts of the motor housing broken away to show the motor and drive shaft.

Each housing 30 or 31 contains a rotary electric motor or other actuator 34 drivingly engaged with a transverse drive shaft 35 supported at the forward end by an apertured bearing wall 40 (FIGS. 2 and 7). The drive shaft 35 includes a drive gear 41 that in turn engages a gear 36 at the end of the main rotational shaft 32. The main shaft 32 is tapered or stepped down toward the gear 36 and includes a radially expanded mounting flange or collar 42 in spaced relation to the inboard end (FIGS. 8-12). The shaft 32 is fitted with a pair of tapered roller bearings 43 that engage the inner surface of the motor housing 30 or 31. An inboard end portion of each main shaft 32 projects outside the motor housing 30 or 31 for connection with the rotatable block 33. As shown in FIGS. 2 and 9-12, the rotatable block 33 is apertured to receive the inboard end of the main shaft 32, which is fastened in place with bolts or the like through the apertured collar 42 and onto the rear surface of the block 33. The main shaft 32 is bored through to include a horizontal bore or channel 44 that extends along its length and the rotatable block 33 includes a corresponding bore or channel 45. The channels are located so that, when the shaft 32 is installed in the rotatable block 33, the channels 44 and 45 are collinear. The housing 30 includes a corresponding aperture that is normally covered by an escutcheon, cover or cap 46. The cap 46 may be removed to open a continuous passageway from the outboard surface of the housing 30 to the inboard surface of the rotatable block 33. Cables may be passed or threaded through this passageway for use in conjunction with for example, a traction harness or other skeletal traction apparatus (not shown).

Figure 5:
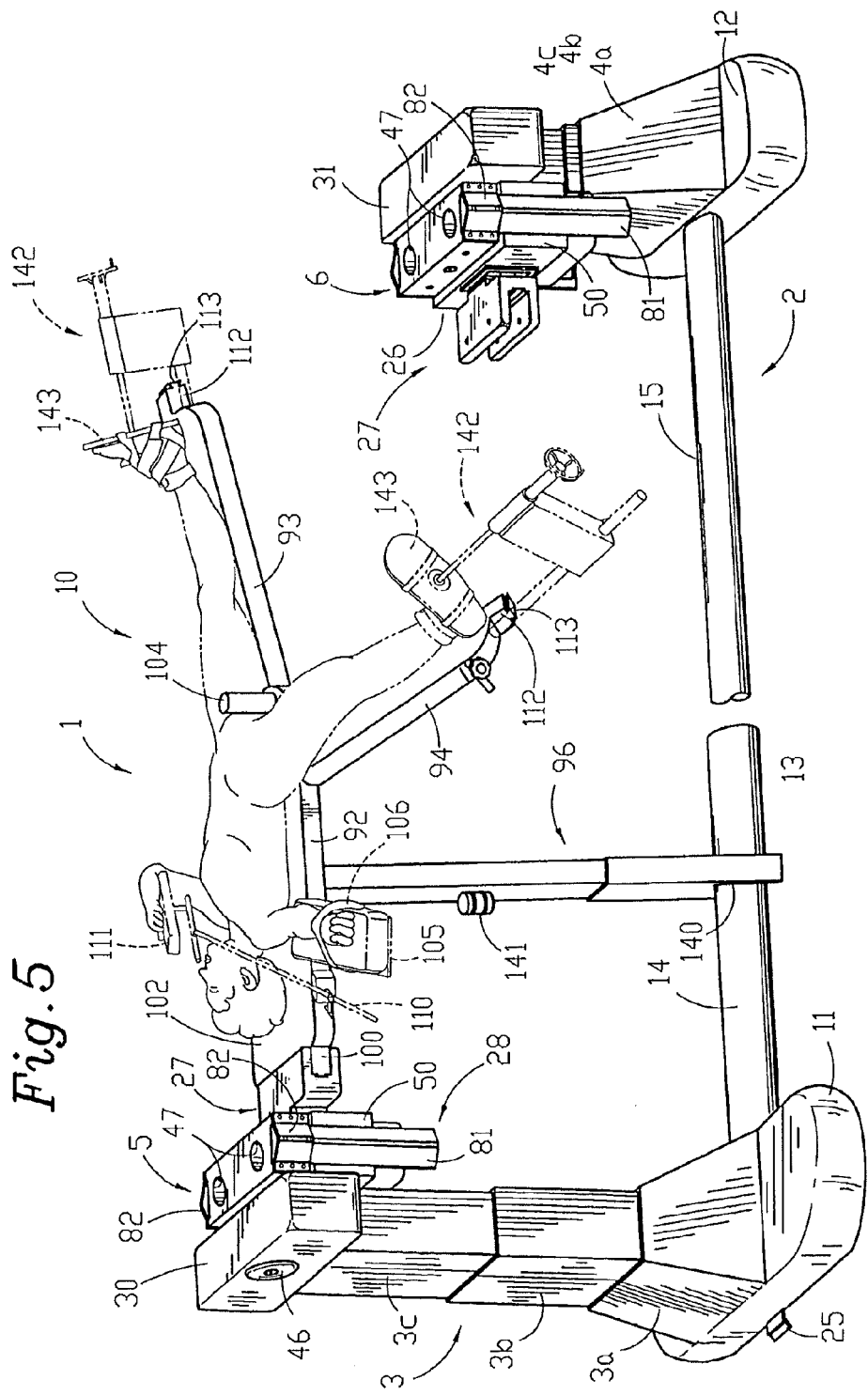
FIG. 5 is a side perspective view of the system showing a patient positioned on the support surfaces in a generally supine position with the leg supports disengaged at the foot end and equipped with traction boots, and showing one of the leg supports pivoted and lowered for abduction of the patient's right leg and to achieve hyperextension of the hip.

As shown in FIGS. 1, 2 and 5, the normally uppermost surface of each rotatable block 33 includes a pair of spaced apertures or slide channels 47 that are sized for receiving a pair of removable elongate riser posts 48 (FIG. 8) for supporting an optional second patient support structure 10a. The riser posts 48 are depicted as having a generally tubular configuration, and each includes a series of vertically spaced apertures 49 for receiving pins 49a for securing the second patient support structure 10a in place at a preselected height in spaced relation to the first patient support structure 10.

The rotation mechanism 26 is operated by actuating the motor 34 using a switch or other similar means. The motor 34 operates to turn or rotate the transverse drive shaft 35 and associated drive gear 41, which engages the gear 36 on the main shaft 32, causing the main shaft 32 to turn or rotate about a longitudinal axis A of the system 10 (FIGS. 1, 2, 7 and 10). The collar 42 of the rotating main shaft 32 is in fixed engagement with and serves to turn or rotate the rotatable block 33. The rotatable block 33 is remotely coupled with and turns or rotates the associated patient support structure 10 via the angulation and separation subassemblies 27 and 28 and the patient support structure 10a via the riser posts 48, to be more fully described hereinafter.

The angulation subassembly or pivotal mount 27 is coupled with the patient support structure 10 for enabling selective angular adjustment of the support structure 10. As best shown in FIGS. 8-12, each angulation subassembly 27 includes a gear box 50 that houses a pivotable nut pivot block 51 that is intercoupled with a pivotable bracket arm 52 that supports a table top or other patient support structure 10 in accordance with a preselected, adjustable angular orientation or pitch. The inboard wall of the gear box 50 is apertured to receive the bracket arm 52, and the outboard aspect is substantially open to permit easy access for maintenance. The floor of the gear box 50 is apertured or punched out to accommodate upwardly projecting attachments to a generally rectangular mounting plate or motor housing mount 53 that is pivotally mounted below the floor of the gear box 50 as well as a drive mechanism for the separation subassembly 28 to be more fully described. Pivot pins or trunnions (not shown) project from the opposite ends of the motor housing mount 53 and are aligned to define a pivot axis that is orthogonal to a longitudinal axis of the system 1. Each trunnion, along with a corresponding bushing, is received in a respective flanged pillow block bearing 54 (FIG. 8) that is fastened to the under surface of the gear box 50. The trunnions enable the motor housing mount 53 to tip or rock slightly to and fro about the pivot axis in response to stresses on the attachments it supports.

As shown in FIG. 8, the motor housing mount 53 has a pair of spaced, side-by-side apertures through the planar surface thereof to respectively receive a DC motor or other suitable actuator 55 within a housing, and a jack or lead screw 56. The motor 55 includes a drive shaft that extends downwardly to engage a motor pulley (not shown). A stepped down lower portion of the lead screw 56 is received within a bearing housing 60 that is fastened to the lower surface of the motor housing mount 53 from below (FIGS. 11-12). The bearing housing 60 contains a pair of angular contact bearings 61 for engagement with the lead screw 56. A further stepped down portion of the lead screw extends downwardly below the bearing housing 60 to engage a pulley 62 driven by a belt 63 that is reeved about the motor pulley. The parts extending below the motor housing mount 53 are covered by a generally rectangular pan or belt housing 64 and the open outboard wall of the gear box 50 is covered by a gear box cover plate 65 (FIG. 10), each held in place by a plurality of fasteners such as panhead screws.

The upper end of the lead screw 56 extends through a clearance slot or aperture in the bracket arm 52 and then through the nut pivot block 51 which is fixedly secured to a lead nut 70. The lead screw 56 is threaded into the lead nut 70. The nut pivot block 51 includes a pair of projecting pivot pins or trunnions (not shown), which are aligned to define a pivot axis orthogonal to a longitudinal axis of the system 1. Each trunnion is received along with a corresponding bushing in a respective flanged pillow block bearing 71 that is fastened by bolts or the like into the upper rearward surface of the bracket arm 52 (FIG. 8). This structure enables the nut pivot block 51 and attached lead nut 70 to tip or rock to and fro to accommodate slight changes in the angular orientation or pitch of the lead screw 56.

The bracket arm 52 has a generally dog-leg configuration and includes an elongate clearance slot 72 positioned lengthwise adjacent the outboard end for receiving the upper portion of the lead screw 56. The lateral surface of the shank of the bracket arm 52 adjacent its inboard end includes a pair of opposed projecting pivot pins or trunnions 73 aligned to define a pivot axis orthogonal to a longitudinal axis of the system 1. Each trunnion 73 is received along with a corresponding bushing in a respective flanged block bearing 74. The bearings are mounted by means of fasteners in partially inset or recessed fashion in corresponding grooves or depressions formed on the inboard surface of the gear box 50.

The distance between the pivot axis defined by the bracket arm trunnions 73 and the pivot axis defined by the trunnions of the motor housing mount 53 is fixed. The distance between the pivot axis of the nut pivot block 51 and the bracket arm pivot axis 73 is also fixed. Thus, alteration of the distance between the nut pivot block 51 and the motor housing mount 53 causes the bracket arm 52 to ride up or down on the lead screw 56. The clearance slot 72 in combination with the pivoting action of the nut block 51 and the motor housing mount 53 accommodates the tilted aspect of the lead screw 56 and permits the outboard end of the bracket arm to ride freely up and down on the screw 56, thus commensurately varying the angular pitch of the patient support structure 10.

The inboard end of the bracket arm 52 extends through the apertured gear box 50 and is configured to form a clamp-like slot or channel 75 for receiving an end of a patient support structure 10. The channel 75 has a generally U-shaped configuration overall when viewed in cross section, however the vertical end wall portion includes a dovetail mortise 80 for mating engagement with a corresponding tenon on the end of the support structure 10. It is foreseen that the inboard end of the bracket arm 52 and the mating outboard end of the support structure 10 may include corresponding vertically oriented apertures for receiving retainer pins or the like. While the bracket arm 52 is depicted and described as having a dog-leg configuration and being of unitary construction, it is foreseen that other shapes may be employed and that the arm 52 may be constructed in two or more sections, with the inner surface of the outboard portion including an outstanding flange for connecting with fasteners to the inboard portion that includes the channel 75.

As shown in FIGS. 9-12, the angulation subassembly 27 is operated by actuating the DC motor 55 to engage the motor pulley (not shown) which in turn rotates the pulley belt 63 that is reeved about the pulley 62 that engages and rotates the lower end of the lead screw 56. It is also foreseen that any of a number of known systems of gears could be employed to rotate the lead screw 56. Rotation of the lead screw 56 pulls the lead nut 70 downwardly on its shaft along with the attached nut pivot block 51, closing the gap between the nut pivot block 51 and the motor housing mount 53. As the lead nut 70 travels down the lead screw 56, the resultant force on the outboard end of the bracket arm 52, which is trapped below the nut pivot block 51, causes the arm 52 to pivot about the trunnions 73 riding on the block bearings 74. The outboard end of the arm 52 is tipped downwardly at the lead screw 56 through the clearance slot 72 and continues to travel down the screw 56, shortening the distance between the bracket arm 52 and the motor housing mount 53. As the bracket arm 52 pivots, the inboard end of the arm containing the channel 75 tips upwardly, varying the angular pitch of the table top 10 to an upraised position. Continued actuation of the motor will tip the table top 10 upwardly as shown in FIG. 11.

Reversal of the motor 55 serves to reverse the direction of rotation of the lead screw 56, which pushes the lead nut 70 upwardly on the screw 56. The attached nut pivot block 51 follows the lead nut and urges the attached outboard end of the bracket arm 52 upwardly along the screw 56 through the clearance slot 72, increasing the gap between the nut pivot block 51 and the motor housing mount 53. As the bracket arm 52 pivots, the inboard end of the arm containing the channel 75 tips downwardly, commensurately varying the angular pitch of the patient support structure 10 to a lowered position. Continued actuation of the motor will tip the table top 10 downwardly as shown in FIG. 12.

In the configuration depicted in FIGS. 11 and 12, each end of the patient support structure 10 may be positioned to subtend an angle of from about 0° (horizontal) to about +25° upward or −25° downward from horizontal. However, it is foreseen that, depending on the configuration of the gear box 50 and components of the angulation subassembly 27, the support structure may be positioned to subtend an angle of up to about +90° upwardly or −90° downwardly from horizontal, that is to say, from an approximately perpendicular upstanding or approximately perpendicular dependent position, with a full range of motion of the table top 10 of up to about 180°.

As shown in FIGS. 8-10, the second patient support structure 10a is supported by a bracket arm 52a having a pair of sockets 58 on the outboard end thereof for receiving the respective riser posts 48. Because the riser posts 48 are received in the slide channels 47 of the rotatable block 33, both the patient support structure 10 and the second patient support structure 10a are rotated by the action of the rotation subassembly 26. However, the angular pitch of the second patient support structure 10a is fixed by the registry of the riser posts 48 within the sockets 58, and will not be varied by the operation of the angulation subassembly 27.

The distance between the patient support structure 10 and second patient support structure 10a may be selectively increased or decreased by the operation of the separation subassembly 28 in order to provide support for a patient during 180° rotation of the structures 10 and 10a by the rotation subassembly 26. The separation subassembly 28 is depicted in FIGS. 1-3 and 8-10 to include first and second pairs of elongate guide bars or rails 81 that adjustably interconnect the rotatable block 33 and gear box 50 at each end of the system 1. The guide rails 81 have a generally triangular configuration in cross section and are installed with the base of the triangle oriented toward the shorter side walls of the rotatable block 33 and gear box 50. The guide rails 81 are connected to the shorter side walls of each rotatable block 33 by guide end brackets 82, that are shaped to receive the guide rails 81. The shorter side walls of the gear box 50 each include a channel or bracket 83 that may be undercut, so that the side walls partially overlap and retain the angular sides of the guide rails 81 in sliding relation within the bracket (FIG. 8). The center portion of the gear box bracket 83 includes a slot for mounting linear bearings (not shown). The inner facing surface of each guide rail 81 includes a normally vertical slot 84 for mounting a linear bearing rail 86 (FIGS. 9, 10), upon which the linear bearings ride.

As best shown in FIG. 8, the floor of the gear box 50 is apertured to receive a housing 85 containing a lead screw 90. The lead screw is connected to a DC motor or other suitable actuator 91 within a motor housing. The motor 91 is fixedly attached to the inside surface of the upper wall of the gear box 50. The lead screw 90 is threaded into a lead nut (not shown) that is fixedly attached to the floor of the gear box 50.

The separation subassembly 28 is operated by actuating the motor by a switch or similar device. The motor 91 rotates the lead screw 90 to pull the lead nut and attached gear box 50 upwardly or downwardly on its shaft, depending on the driving direction of the motor 91. The gear box 50 travels upwardly or downwardly on the bearing rails 86 attached to the guide rails 81, thus raising and lowering the attached patient support structure 10 with respect to the rotatable block 33. Where a second patient support structure 10a is attached by means of riser posts 48 to the rotatable block 33, the upward and downward travel of the gear box 50 serves to shorten and lengthen the distance between the two patient support structures 10 and 10a.

The horizontal support assemblies 5 and 6 support a table top 10 and optional top 10a or other suitable patient support structure such as, for example, open frames, slings or bolsters or combinations thereof. A top 10 suitable for surgery is depicted in FIG. 14 to include a patient body support board 92 coupled with first and second patient leg support boards 93 and 94 by a pair of lockable universal or polyaxial joint assemblies 95 and a dependent pillow support structure 96. FIGS. 8 and 9 depict an optional second support board 92a of open frame construction.

The body board 92 is of unitary construction and is sized to support the head and body of a patient except for the legs. The body board 92 includes an elongate rectangular outboard bracket-engaging section 100 having a dovetail tenon 101 sized for snug sliding reception within the dovetail mortise 80 in the bracket arm channel 75 (FIG. 12). The bracket-engaging section 100 is joined to a generally rectangular center section 102 having four slightly relieved corners (FIG. 1). An elongate perineal section or leg 103 projects from the inboard end of the center section 102 and an upright perineal post 104 is removably mounted adjacent the inboard end of the perineal leg 103. The perineal post 104 is preferably constructed of a radiolucent material to permit imaging. The post 104 may have a generally cylindrical configuration as depicted, or it may be constructed in any other suitable shape for supporting engagement with the perineal region of a patient.

As shown in FIG. 5, the body board center section 102 may serve as a stage for attachment of certain optional and removable accessories. For example, a pivoting padded arm board having strap-type restraints 106 may be employed for lateral positioning of the patient's arm. A cross arm support structure 110 including an elevated arm board 111 may be employed for raised, spaced positioning of the patient's arm with respect to the body.

The first and second patient leg boards 93 and 94 are rotatably attached to the body board center section 102 in spaced relation to the perineal leg 103 by first and second polyaxial joint assemblies 95. The leg boards 93 and 94 each have a generally elongate rectangular configuration with relieved corners. The outboard ends each include a bracket-engaging section 112 having a dovetail tenon 113 for reception within the dovetail mortise 80 in the bracket arm channel 75. The inboard end of the foot end bracket arm 52 and each of the bracket-engaging sections 112 are vertically apertured to receive a pair of spaced removable pins 114 for securing the leg boards 93 and 94 in place (FIG. 1).

Figure 6:
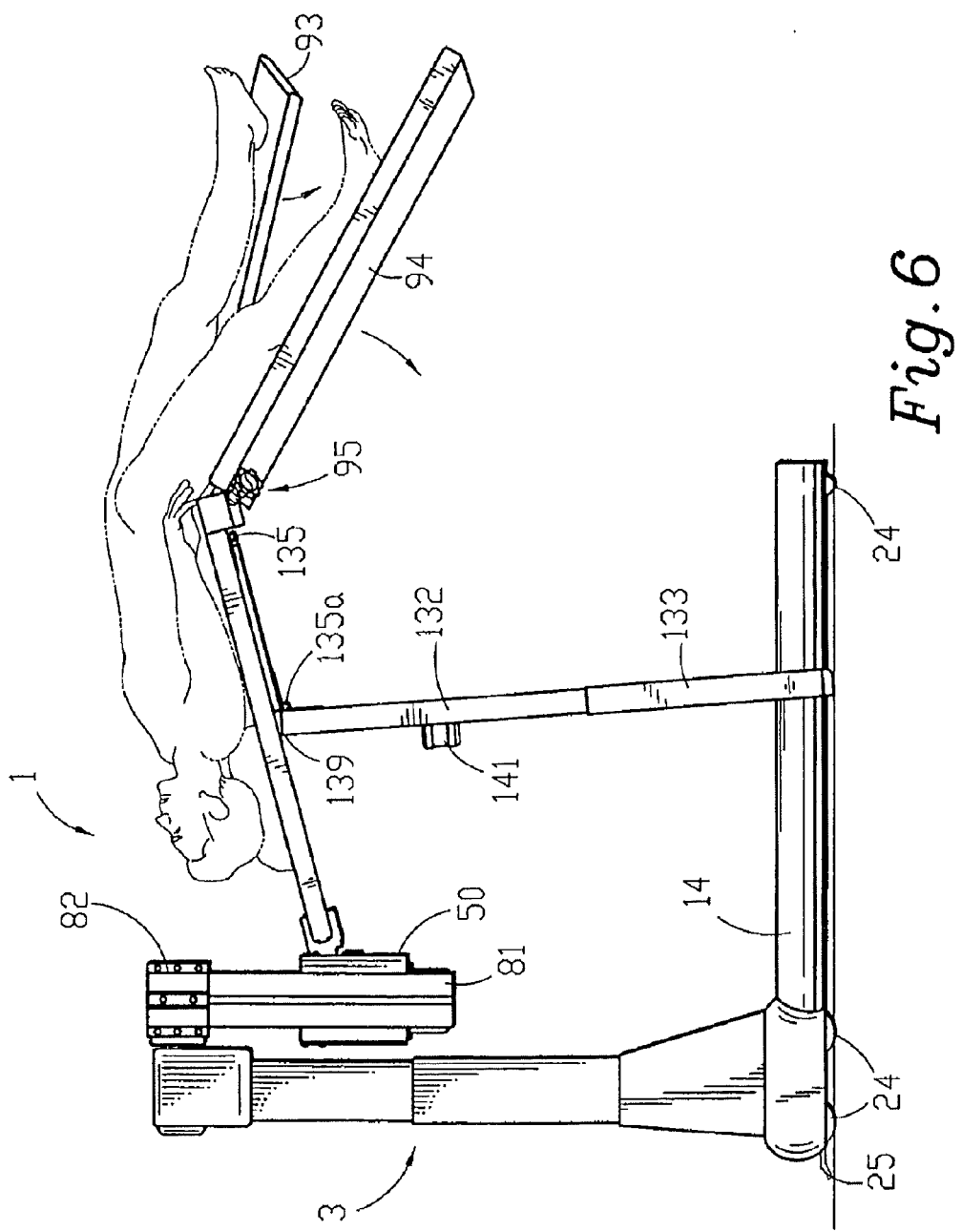
FIG. 6 is a side elevational view of the system similar to that shown in FIG. 5, with the second support column and associated base rail removed, and the patient's head and feet lowered to leave the hip area elevated for disarticulation, such as is needed for minimally invasive total hip replacement.

The body board 92 and leg boards 93 and 94 are constructed of a radiolucent material to permit patient imaging during use. Although depicted in FIGS. 1-5 as being of equal length, those skilled in the art will appreciate that the body board 92 may be constructed to have greater length than the leg boards 93 and 94 or vice versa to enable positioning of a patient so that articulation of the leg boards 93 and 94 will occur adjacent the superior aspect of the iliac crest in order to facilitate disarticulation of the hip and hyperextension of the lumbar spine as shown in FIG. 6. In addition, the board modules 92, 93 and 94 may be selectively replaced with other modules having different lengths or construction details, such as open frames, slings or bolsters.

FIGS. 13-17 show details of the polyaxial joint assemblies 95 that interconnect the body board 92 with the leg boards 93 and 94 to enable adjustment of the angular pitch in nearly all directions. The joint 95 includes a housing 115 having a generally spherical interior socket 116 that receives a generally spherical ball member 120. The outer rear wall of each housing 115 includes an orthogonally projecting shaft 121 that is installed within a corresponding bore in the inboard margin of the body board 92. The ball 120 is mounted on a shaft 122 that is installed within a corresponding bore in the inboard margin of a leg board 93 or 94. The housing 115, which may be constructed of radiolucent carbon fiber or other suitable material, includes a pair of spaced threaded apertures 123 for receiving a pair of pads or set screws 124, each of which has a correspondingly threaded stem and is equipped on the outboard end with a handle or finger knob 125. The apertures 123 are positioned so that the installed set screws 124 will subtend an angle of about 45° from an axis B defined by the housing shaft 121 as shown in FIG. 17. The stem of each set screw 124 terminates in an engagement tip 130 that is arcuately configured in a generally concave conical shape for mating engagement with the spherical surface of the ball 120 for cooperatively securing the ball against the inner surface of the socket 116 (FIGS. 13 and 14). While a ball and socket type joint assembly has been depicted and described herein, those skilled in the art will appreciate that any lockable universal joint, such as, for example, a lockable gimbal joint may also be employed to enable polyaxial rotation of the leg boards 93 and 94.

The intermediate support structure 96 shown in FIGS. 1 and 3 to depend between the outboard ends of the leg boards 92 and 93 with the inboard end of the body board 92. The structure 96 is designed to convert from a pillow support to a brace when it is positioned as shown in FIGS. 4 and 5. The structure 96 includes a pivotable first support element 131, telescoping second and third support elements 132 and 133 and a pair of dependent spaced wire supports 134. The elements 131, 132, 133 and wire supports 134 depend from the patient support top 10 in end-to-end relation to form a shelf which may be used for supporting an optional pillow (not shown) that is configured to extend upwardly to fill the space between the leg boards 93 and 94.

The first element 131 is generally rectangular and planar, and is equipped at each end with a hinge 135 or 135a (FIG. 3). Hinge 135 pivotally connects one end to the lower surface of the body board 92. Hinge 135a pivotally connects the opposite end to the second support element 132. The hinges 135 and 135a enable pivotal movement of the element 131 from the dependent position shown in FIG. 1 to a position parallel and adjacent the lower surface of the body board 92 shown in FIG. 4.

The generally planar rectangular second element 132 is joined at one end to the first element 131 in a generally perpendicular orientation. The opposite end of the second support element 132 is slidingly and telescopically received within a hollow end of the third support element 133. The hollow end of the third element 133 also includes conventional rack and pinion gear structure (not shown) similar to that within the crossbar 13 to permit locking telescoping adjustment of the length of the two coupled elements when in the upright positions shown in FIGS. 4-6. The third support element 133 is generally planar and rectangular except for a notch 140 at the outboard end (FIG. 1). The notch 140 is sized to receive the first rail 14 of the crossbar 13 when the third support element 133 is in an upright position shown in FIGS. 4-6.

The wire supports 134 comprise two spaced sets of articulated wire sections 134a, 134b, and 134c, each of which sets depends from a respective foot board 93 or 94. It is foreseen that a stabilizing crossbar may also be included at the junction of the first and second sections 134a and 134b or other suitable location. The lower sections 134b and 134c are pivotable upwardly from the position shown in FIG. 4 to form a generally triangular releasable loop foot (FIG. 3) that is sized to receive an outboard end corner of each of the leg boards 93 and 94.

In order to achieve unrestricted positioning of a patient's legs, the leg boards 93 and 94 can be disengaged from the angulation subassembly 27 and raised, dropped down or rotated nearly 360° in all directions (FIGS. 5 and 6). As shown in FIGS. 3-6, it is desirable to first disengage the support structure 96 from its pillow-supporting position to form an upright brace for providing additional support for the body board 92. This is accomplished by unfolding the loop foot portion of support bracket 134 so that it disengages the outboard corners of the pillow shelf element 133. The top ends of the wire supports 134 can then be disengaged from the foot boards 93 and 94 and removed for storage. The first support element 131 is rotated about the hinge 135 to the position shown in FIG. 4. As the first support element 131 is rotated the second and third support elements rotate downwardly and about the hinge 135a. The rack and pinion gear system is actuated by the motor 141 to urge the second support element 132 outwardly from its telescoped position within the third support element 33, thereby elongating the support until the slot 140 engages the crossbar rail 14 in straddling relation. It is foreseen that an elastomeric gasket 139 may be provided between the now upstanding end of the second support element and the lower surface of the body board 92 to cushion against any flexing or tilting of the body board 92 which may occur when the foot boards are released from the angulation subassembly 27. Similarly, the floor engaging corners of the support element 133 may also be equipped with elastomeric feet to facilitate snugging of the brace 96 against the body board 92 and to prevent any slippage of the support element 133 along the surface of the floor.

Once the pillow support structure 96 has been converted to an upright brace as shown in FIG. 4, one or more of the leg boards 93 and 94 may be released from the bracket arm channel 75. One or more of the pins 114 is released and the bracket engaging leg board tenon 113 is slidingly disengaged from the bracket mortise 80 (FIGS. 1 and 5). If both of the leg boards 93 and 94 are released, the floorlock foot lever 25 and the telescoping cross bar rails 14 and 15 may be completely disengaged, leaving the inboard end of the rail 14 supported by the wheel 24 (FIG. 6). This frees the disengaged second horizontal support assembly 6 and its attached upright support column 4, which may be wheeled out of the way. In this manner, access by the surgical team and its equipment to the midsection and lower limbs of the patient is greatly enhanced.

As shown in FIG. 5, an optional leg spar assembly 142 may be attached to the free end of each leg board 92 and 93 for mounting a traction boot 143 or cable (not shown). The leg boards 93 and 94 may each be rotated about one of the ball joints 95, by rotating the finger knob 125 counter clockwise to release the ball 120 within the socket 116. For example, as shown in FIG. 6, the right leg board 94 may be dropped down and tilted laterally or medially with respect to a longitudinal axis to disarticulate the hip of the patient. When the desired angular orientation or pitch of the patient's leg is achieved, the respective finger knob 125 is rotated clockwise to engage the ball against the surface of the socket 116 and secure the leg board 92 or 93 in place.

The system 1 of the invention has been described as actuated by a series of electric motors 23 (vertical translation of support columns 3 and 4 and lateral translation of rack and pinion 21 and 22), 34 (rotation subassembly 26), 55 (angulation subassembly 27), 91(vertical translation of linear guide rail subassembly), and 141 (intermediate support structure 96). Cooperatively these motors form a coordinated drive system to raise, lower, tilt and rotate the patient support structures and to disengage the second support column 4 from the system 1. Actuation of the motors is coordinated by the controller 29, including computer software which may be part of an integrated guidance system that coordinates and controls other devices such as a robotic surgical arm, imaging, monitoring and/or heated or cooled gas and fluid delivery, as well as temperature and/or pressure point management devices. The software may include preset routines for positioning components in preselected positions. In addition, the software may include the capability of fine tuning any aspect of the configuration of the system 1. For example, as the motor 23 is actuated to lower the head and foot end support columns 3 and 4, the motor 91 may also be selectively actuated to lower the body board 92 with respect to the rotatable block 33 while each of the motors 55 are also actuated to tip the body board 92 upwardly and the opposed leg boards 93 and 94 downwardly in accordance with the new angle subtended by the support columns 3 and 4 to a position in which the hips of the patient are above both the head and the feet. It is also foreseen that in lieu of the system of coordinated electric motors described herein, a hydraulic or pneumatic system could be employed.

In use, the horizontal support assemblies 5 and 6 may be positioned in a horizontal orientation and at a convenient height to facilitate transfer of a patient onto the support surface 10. The patient is positioned in a generally supine position with the head, torso and lower body except for the legs on the body board 92 outboard of the perineal post 104, and with one leg on each of the leg boards 93 and 94. Arm boards 105 and 111 may be attached to the body board 92 as necessary, and the patient's arms arranged thereon and restrained using the straps 106.

Figure 23:
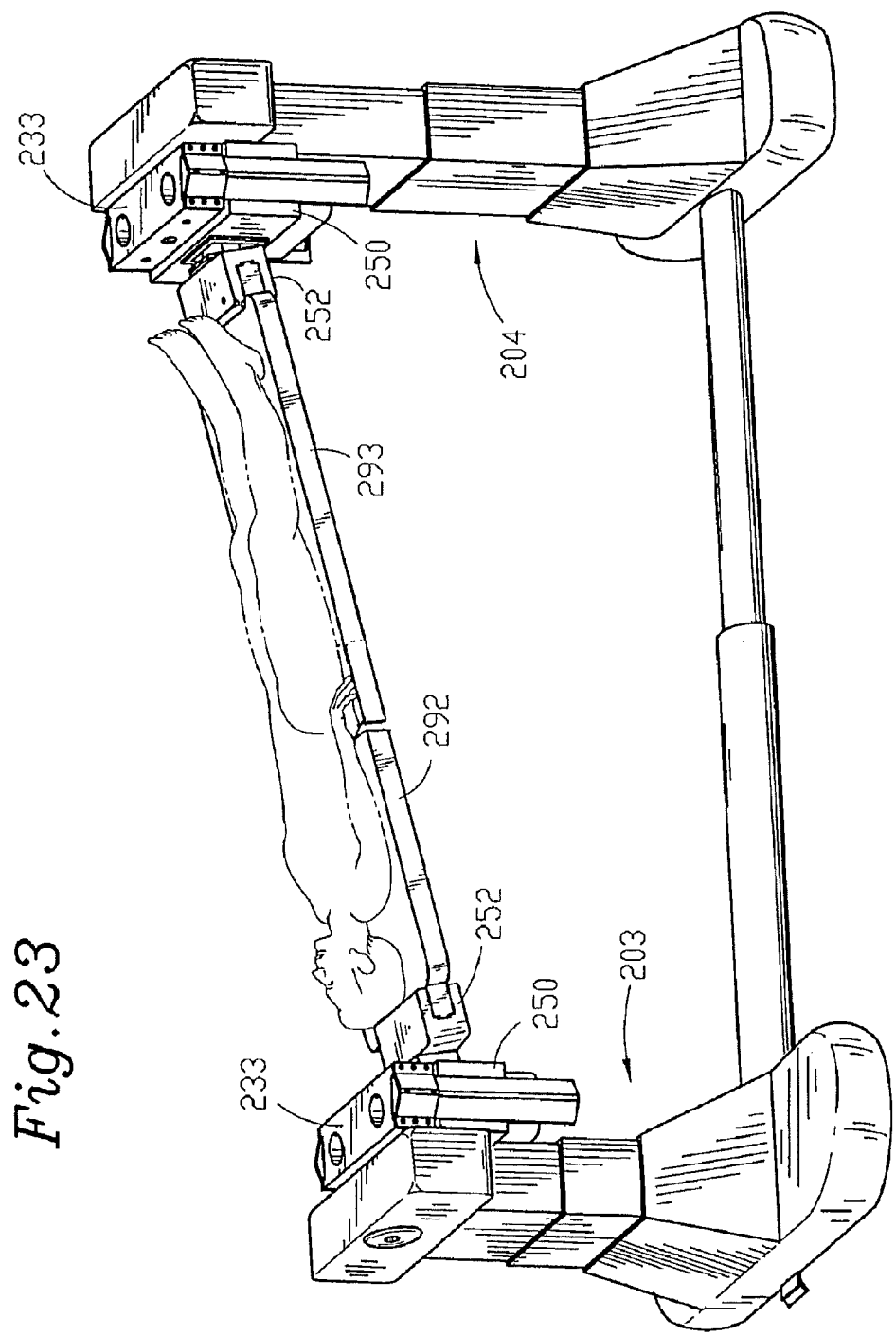
FIG. 23 is a side perspective view similar to FIG. 22, with first column lowered to place the patient in Trendelenburg's position.

The patient may be tilted to a Trendelenburg position (as shown in FIG. 23), or a reverse Trendelenburg position in which the head is raised above the feet, by actuating the motors 23 and 55 to selectively lower a selected support column 3 or 4 and adjust the angulation of the body board 92 and leg boards 93 and 94. Once suitably restrained, the patient may be rotated or rolled from the supine position to a clockwise or counter clockwise laterally tilted position by actuating the motors 34 to rotate the blocks 33.

One or more of the leg boards 92 and 93 may be disengaged and the patient's legs positioned for example, for hip surgery, by converting the intermediate support structure 96 from its pillow-supporting configuration to a central support column as shown in FIG. 4 by disengaging the wire supports 134, rotating the first support element 131 about the hinges 135 to its horizontal position and actuating the motor 141 to extend the support elements 132 and 133 to engage the rail 14. The wire supports 134 are removed and the pins 114 are removed from the bracket arm 52. The bracket engaging section 112 of each of the leg boards 93 and 94 is slid out of the channel 75 by laterally rolling or rotating the respective leg board about the respective polyaxial ball joint 95. This is accomplished by manually turning the finger knob 125 through the sterile drapes to disengage the set screw 124 from the ball 120 and permit free rotation of the ball within the socket 116.

The foot end separation assembly motor 91 may be actuated to raise the gear box 50 to its highest position on the guide rails 81 and the motor 23 may be actuated to lower the foot end support column 4 to its lowest position. The foot end floorlock foot lever 25 is next disengaged to free the foot end support column 4, while the head end support column 4 remains locked down. The motor 23 is actuated to urge the rack and pinion 21 and 22 to commence withdrawal of the rail 15 from its telescoped position within the rail 14 and thereby lengthen the crossbar 13 to its fully extended position. The rack and pinion locking assembly 20 is then released either manually or by means of a switch so that the entire second upright support column 4 with its horizontal support assembly 6 and attached rail 15 may be wheeled out of the way to provide the surgical team and equipment with free access to the pelvis as well as to the hip joints and legs of the patient from both a medial and lateral approach.

Once the leg boards 93 and 94 have been rotated laterally, away from the longitudinal axis of the system 1, they may be positioned as shown in FIG. 6, with the outboard ends tilted upwardly or downwardly and angled laterally or medially. The leg boards 93 and 94 are secured in place in the selected angular orientation by manually tightening each of the finger knobs 125 through the sterile drapes until the engagement tips 130 lock the ball 120 against the inner surface of its socket 116. Leg spar assemblies 142 may be installed on the leg boards 93 and/or 94 and the patient's feet may be fitted with traction boots 143.

Figure 18:
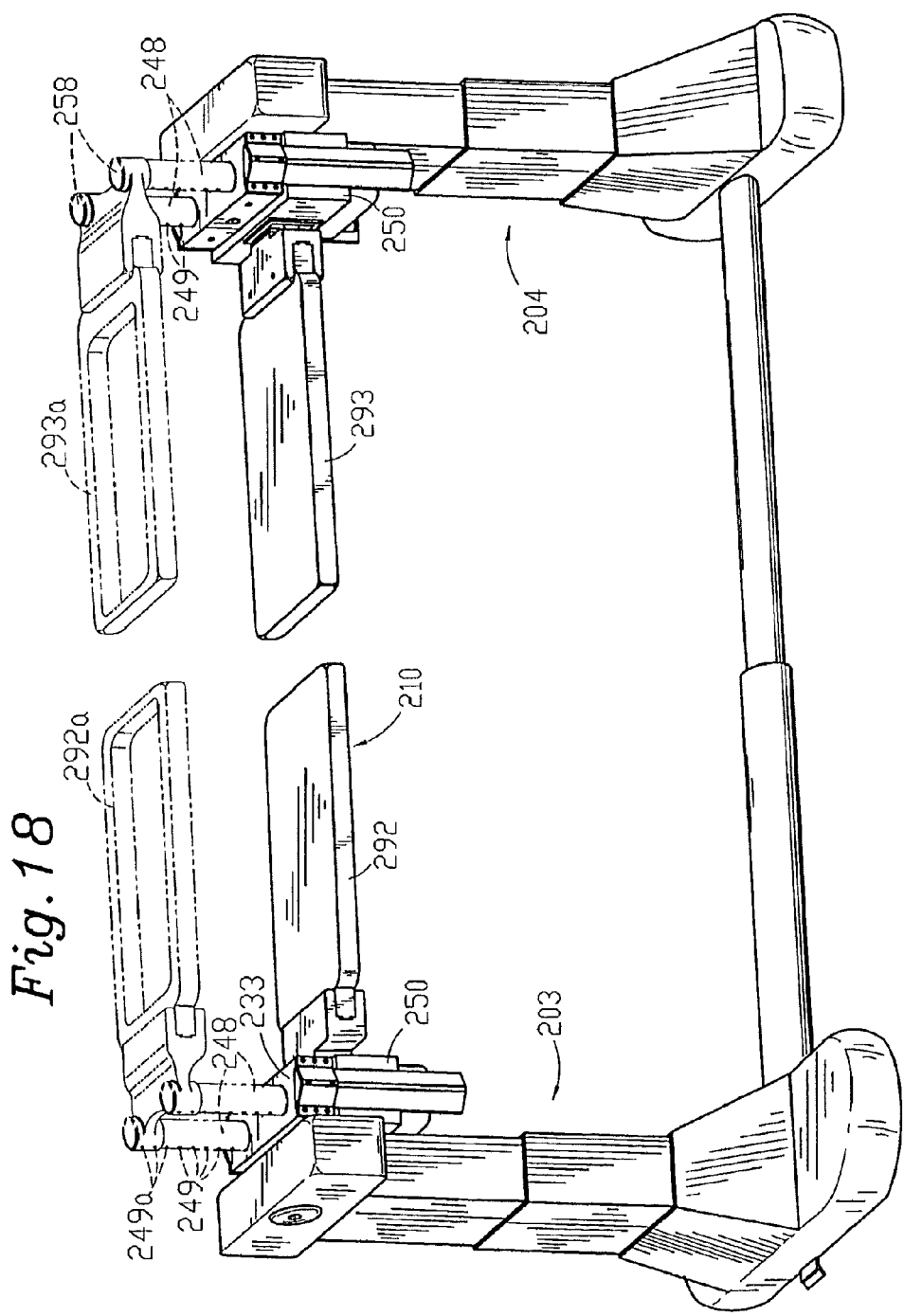
FIG. 18 is a side perspective view of an alternate modular multi-articulated patient support system having a first pair of patient support structures, with a second pair of support structures shown in phantom.
Figure 24:
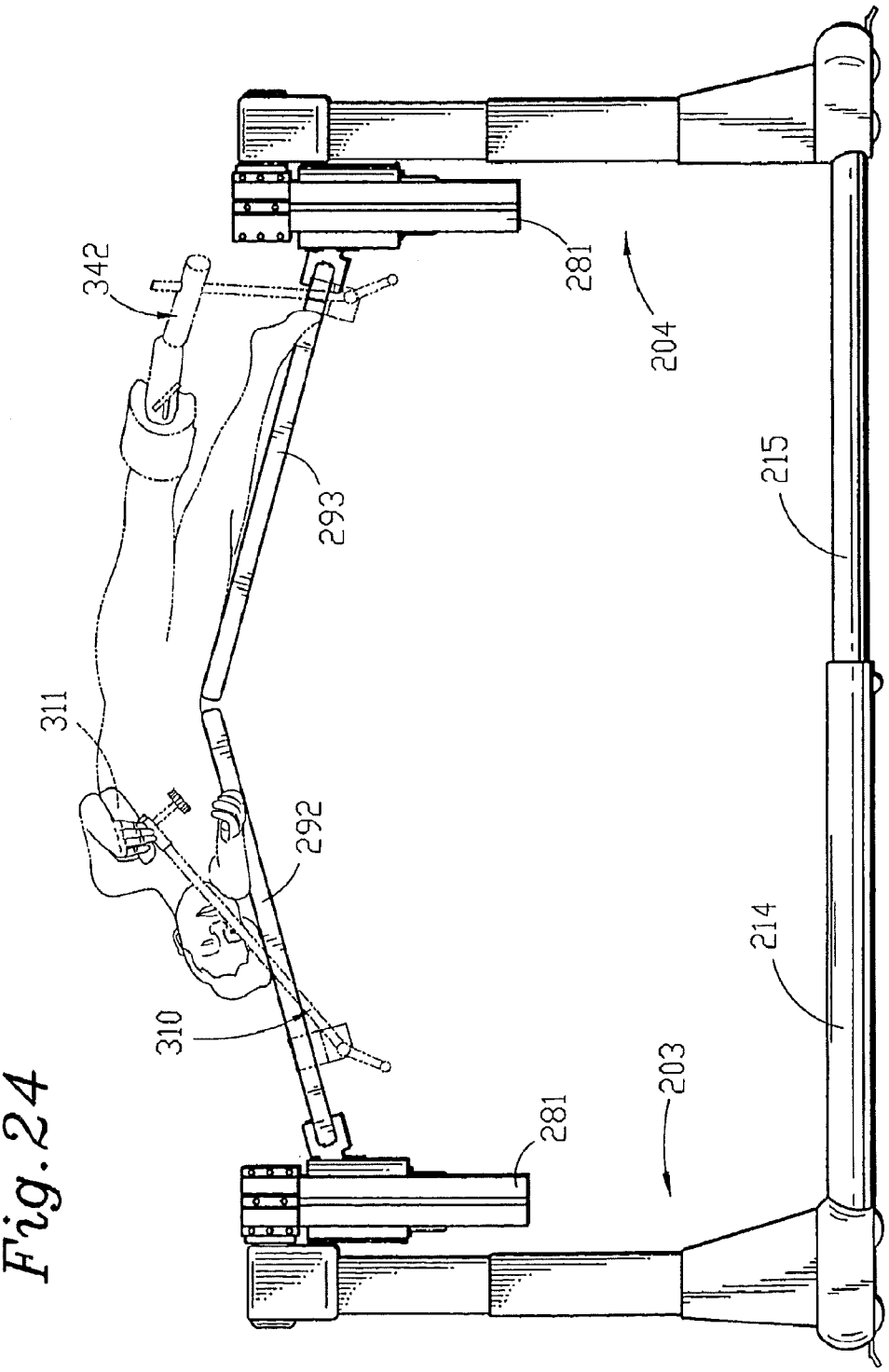
FIG. 24 is a side perspective view of the system showing a patient in a lateral position on two centrally raised support surfaces, with an optional leg spar and patient arm transfer board shown in phantom.
Figure 25:
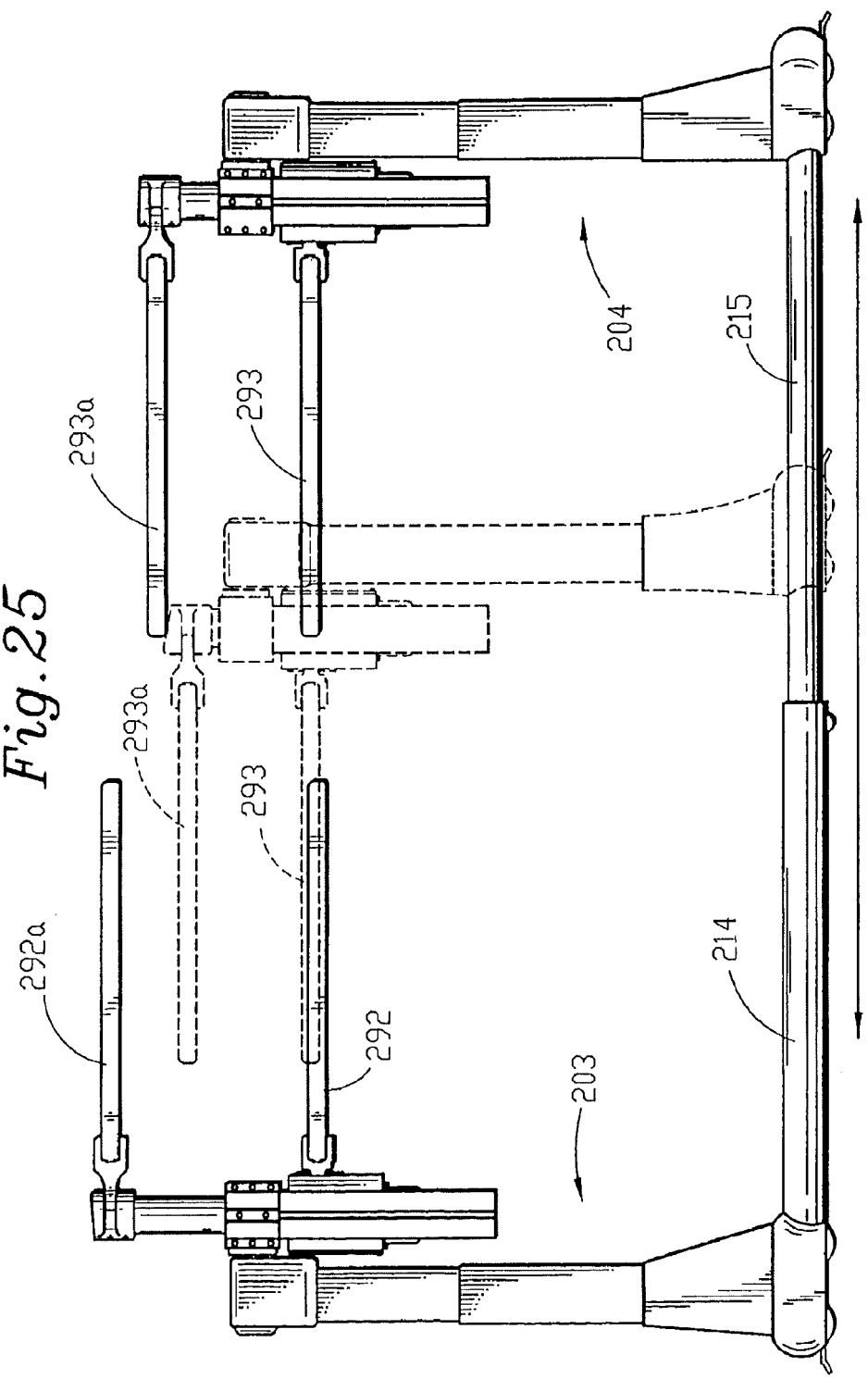
FIG. 25 is a side elevation of the system with both first and second pairs of support structures in place and showing in phantom the foot end column and associated patient support structures shifted toward the head end.
Figure 26:
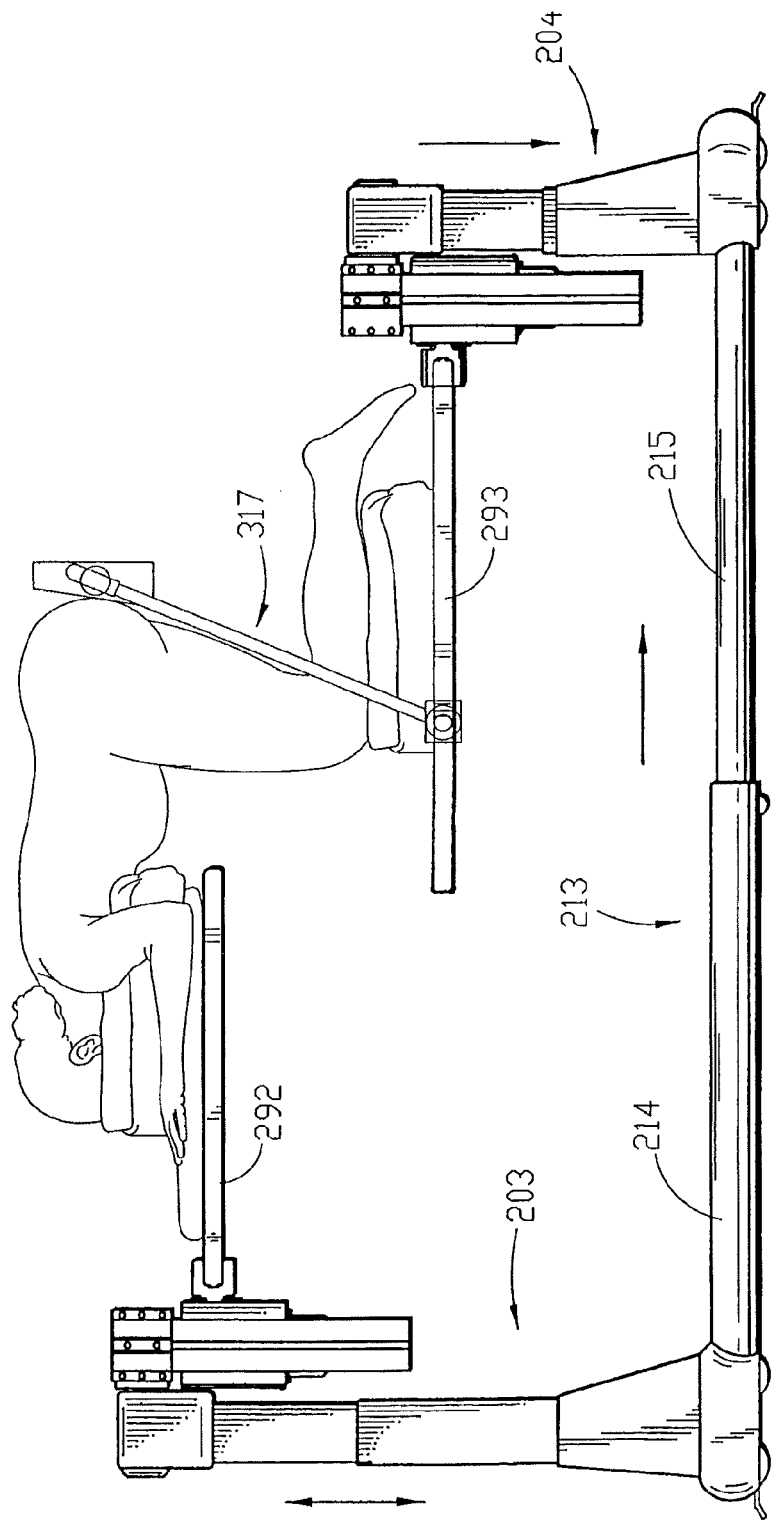
FIG. 26 is a side elevation of the system with the head end patient support structures in an elevated position and the foot end patient support structures in a lowered position supporting a patient in a 90°/90° kneeling prone position.
Figure 27:
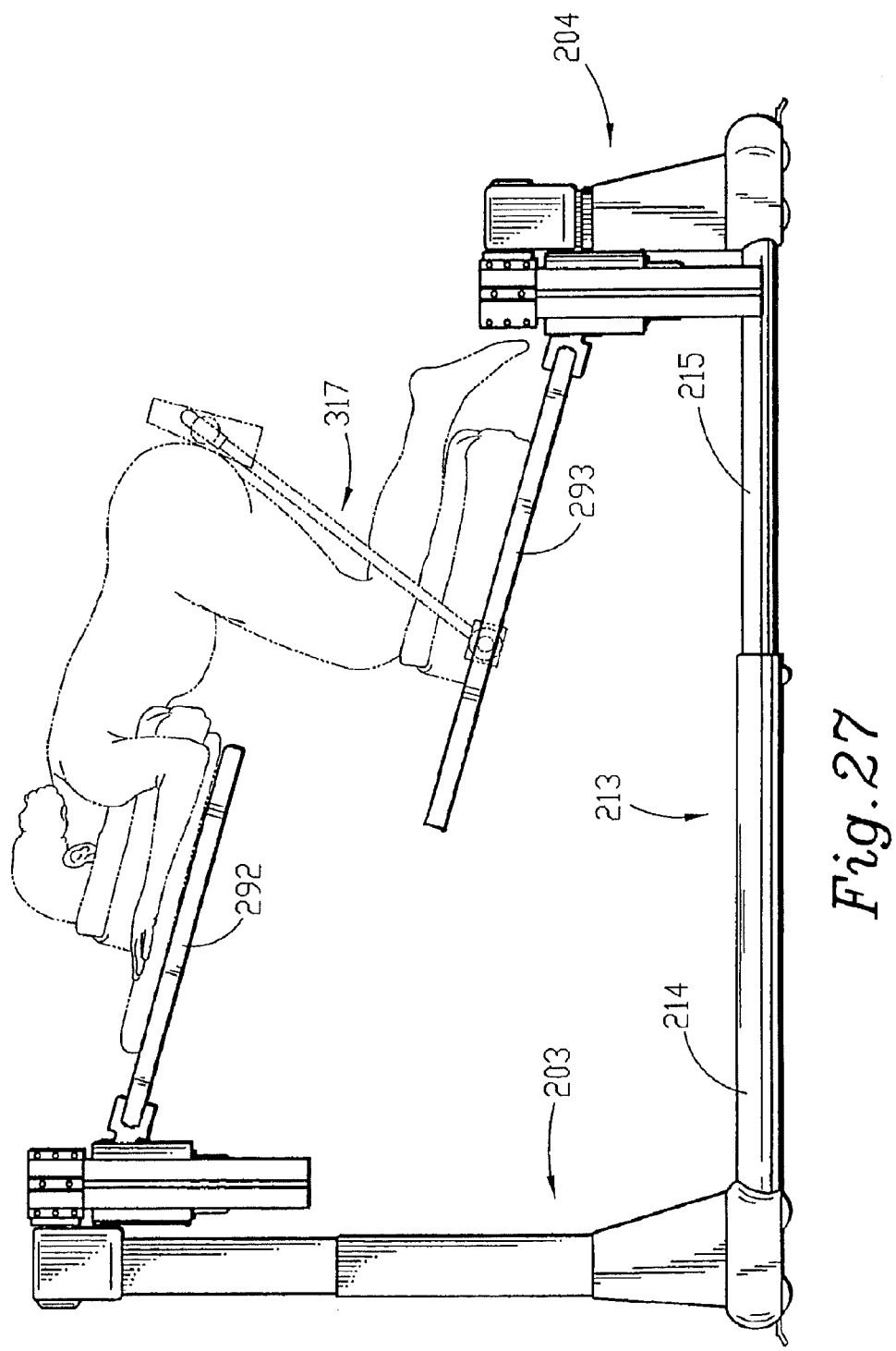
FIG. 27 is a side elevation similar to FIG. 26, with the first column raised, the second column lowered and the associated head and foot end patient support structures pivoted and supporting a patient in a 90°/90° kneeling prone position approximately 30° from horizontal.

A second embodiment of the patient support system of the invention is generally designated by the reference numeral 201 and is depicted in FIGS. 18-27 to include a base 202, support columns 203 and 204 and horizontal support assemblies 205 and 206 including rotation subassemblies 226, angulation subassemblies 227 and linear guide rail or separation subassemblies 228 substantially as previously described. The patient support structure 210 includes a pair of body boards 292 and 293, depicted as surgical tops and open frames (FIG. 18), although as previously discussed, other suitable structures such as slings, bolsters or a combination thereof may be employed. The boards 292 and 293 each include bracket engaging sections 300 that are received within channels 275 in brackets 283 attached to gear boxes 250. The inboard ends of the body boards 292 and 293 are free so that they may be independently raised and lowered by the support columns 203 and 204 (FIG. 26). The distance between the inboard ends may be increased or decreased by actuation of a rack and pinion in the crossbar first section 214 to telescopically receive a portion of the second crossbar section 215, shortening the horizontal length of the crossbar 213 to achieve the overlapping positioning of the body boards 292 and 293 depicted in FIG. 25. The body boards 292 and 293 need not be uniform in size and may vary in length and thickness (in which case correspondingly sized brackets 252 are employed). In particular the foot end board may be longer than the head or torso board, in which case the angulation of the boards when the ends are proximate would occur at approximately the waist of the patient. As shown in FIG. 18, a frame type patient support 210 may be employed in conjunction with a body board type of support to support a patient, or a pair of frame type patient supports may be employed in lieu of body boards. It is foreseen that the free ends of the body boards 292 and 293 may be spaced substantially apart and a third body board (not shown) may be interconnected by means of additional brackets 252 on the free ends of the boards 292 and 293 in order to provide a substantially elongated patient support surface 210. It is also foreseen that the boards 292 and 293 may be brought into contact with each other in stacked relation, for example for use with children or in small rooms in order to reduce the overall length of the system 201. Since such an arrangement necessarily provides a double thickness patient support structure, the resultant structure has a greater load bearing capacity. The angulation of each of the body boards 292 and 293 may also be individually adjusted by the angulation subassembly 227 as shown in FIGS. 23, 24 and 27 and the adjustment may be coordinated to achieve complementary angulation for positioning of a patient, for example with the inboard ends of the body boards 292 and 293 upraised as shown in FIG. 24.

As shown in FIGS. 18-21 and 25, the system 201 is designed to include an optional and removable second pair of patient support structures 210*a* attached by brackets 252 coupled with riser posts 248. The support structures 210*a* are depicted in FIGS. 8 and 18 as first and second generally rectangular open frames 292*a* and 293*a* and as surgical tops in FIGS. 19-21 and 25. Those skilled in the art will appreciate that the patient support structures 210 and 210*a* may comprise conventional surgical table tops and open frames as described or any other structure capable of supporting a patient, whether directly or in association with pads, slings, cables, brackets, pins or in any other suitable manner. Any of the board modules 292, 292*a*, 293 and 293*a* may also be removed and replaced by modules of alternate construction during the course of a medical procedure as may be desirable. The body boards/frames 292*a* and 293*a* include bracket engaging sections 300*a* that are received within channels 275 in corresponding brackets 283*a*. The outboard portion of each bracket 283*a* includes a pair of sockets 258 for receiving a pair of riser posts 248. The riser posts 248 include a series of vertical apertures 249 for receiving pins 249*a* for holding the riser posts 248 in place at a preselected height or distance above the rotatable blocks 233.

The body boards and/or frames 292 and 292*a* also be equipped with optional and removable accessories such as a cross arm support 310 and arm board 311 and the body boards and/or frames 293 and 293*a* may also be equipped with accessories such as leg spar assemblies 342 as shown in FIG. 24 or other support assemblies such as the kneeler assembly 317 shown in FIG. 27

In use, the second pair of support structures 210*a* are installed by sliding the sockets 258 over the corresponding riser posts 248 and fastening in place with pins 249*a* through the apertures 249 as shown in FIG. 18. The rotation subassembly 226 is actuated to operate as previously described for rotating the blocks 233 along with the attached frames 292*a* and 293*a* and the gear boxes 250 along with the attached body boards 292 and 293 about the longitudinal axis of the system 201 into the 180° position shown in FIG. 19.

Figure 19:
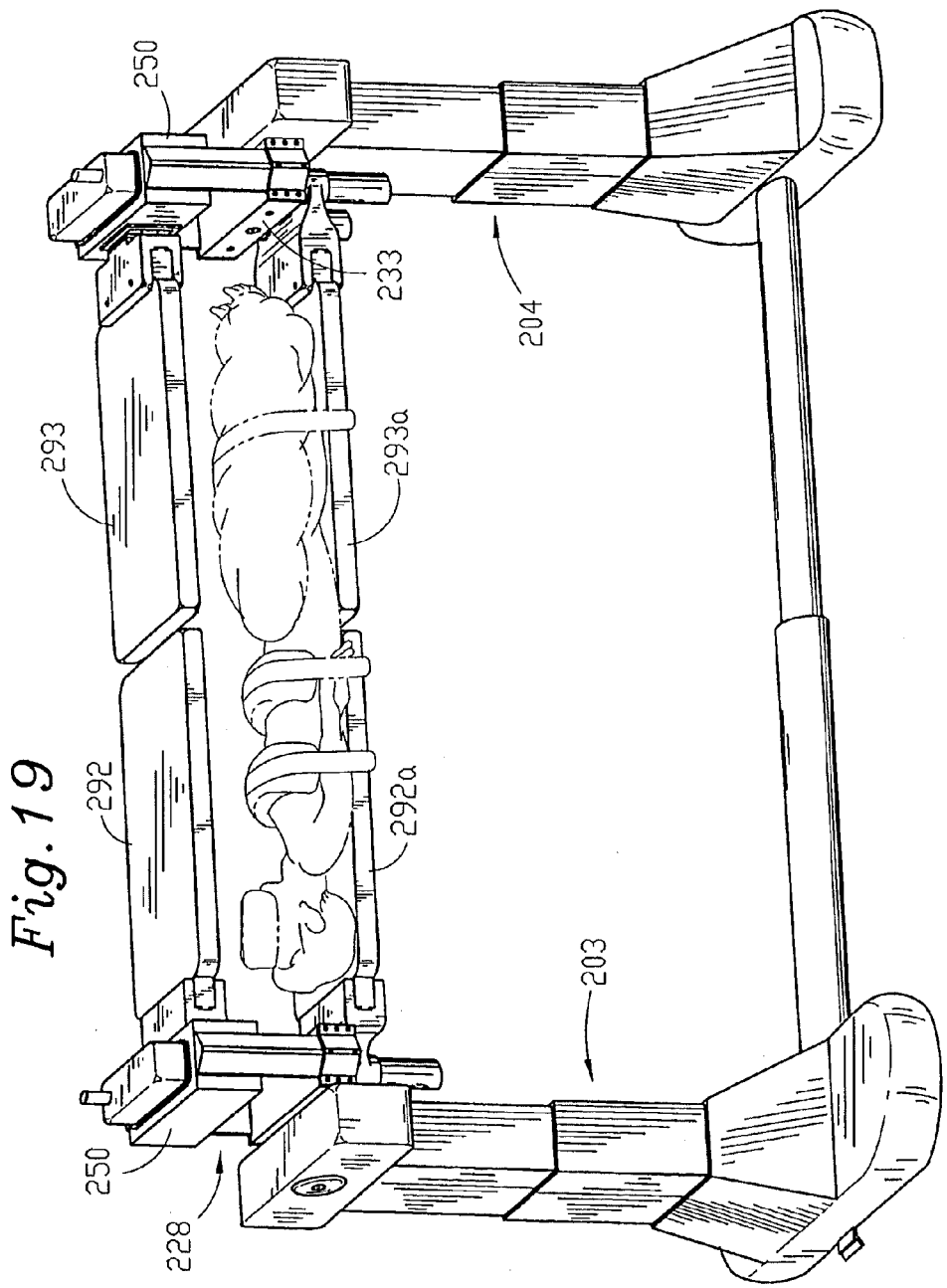
FIG. 19 is a side perspective view of the system shown in FIG. 18 showing the patient support structures rotated 180° and with the first set of patient support structures in a raised position, a patient shown in phantom in a supine position and secured to the second set of patient support structures.
Figure 20:
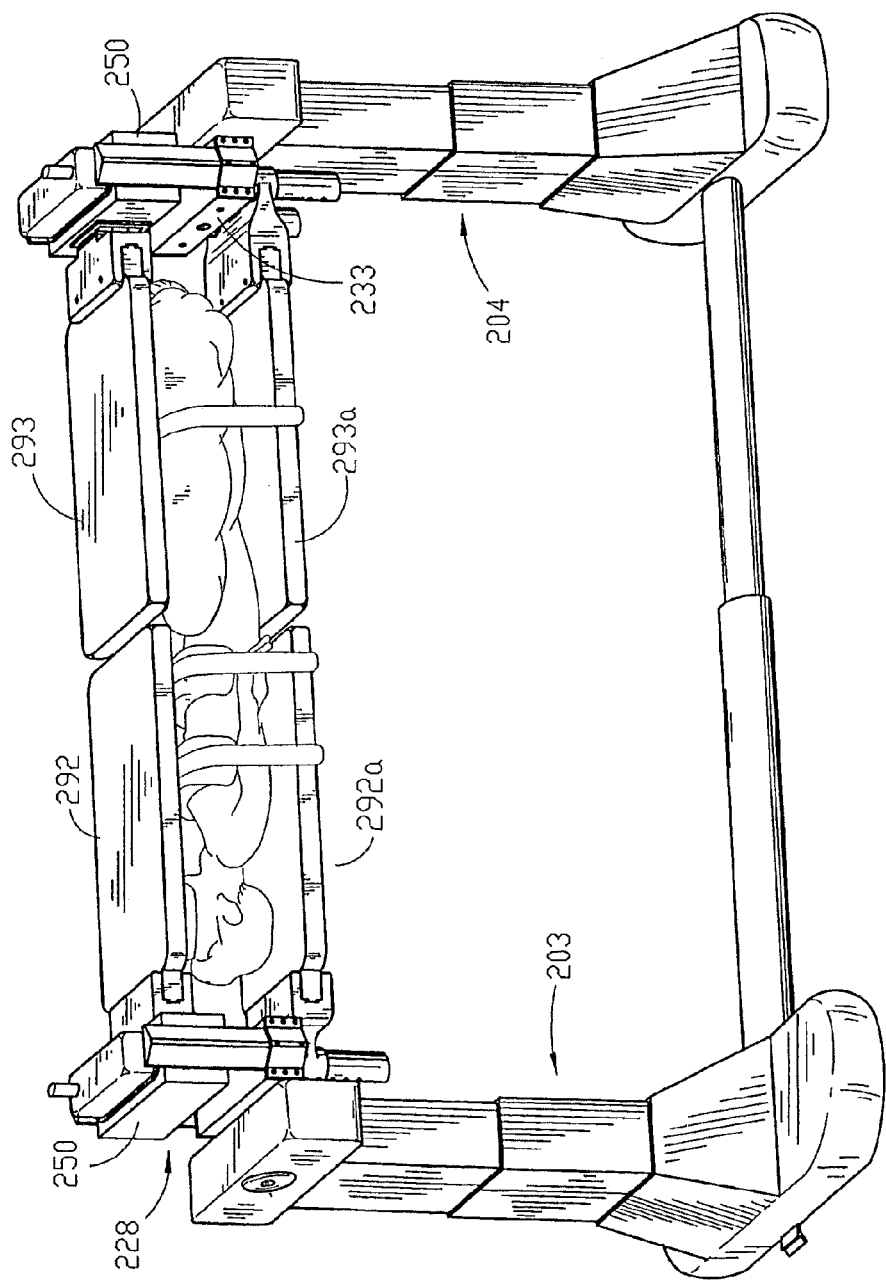
FIG. 20 is a side perspective view similar to that of FIG. 19 with the first set of patient support structures in a lowered, position approaching contact with a patient.

The separation subassembly 228 is actuated to operate in the manner previously described to urge the gear boxes 250 along with the attached body boards 292 and 293 along the guide bars 281 and into the upraised position shown in FIG. 19 to provide ample space for transfer and positioning of a patient. The overall height of the system 201 may be adjusted for convenient patient transfer by actuating the telescoping action of the support columns 203 and 204. The upright support columns 203 and 204 raise and lower the patient support structures 210 and 210*a* in tandem, and cooperate with the separation subassembly 228 to set the patient support structures 210 and 210*a* at a preselected height with respect to the floor and a preselected separating distance with respect to each other.

A patient is next transferred onto the support boards 292*a* and 293*a* and a protective guard 294 is positioned over the face and restraint straps 295 positioned at strategic points along the patient's body and snugged against the body boards 292*a* and 293*a*. The separation subassembly 228 is actuated to urge the gear boxes 250 closer to the rotatable blocks 233, decreasing the distance or separation between the patient support boards in the position shown in FIG. 20.

Figure 21:
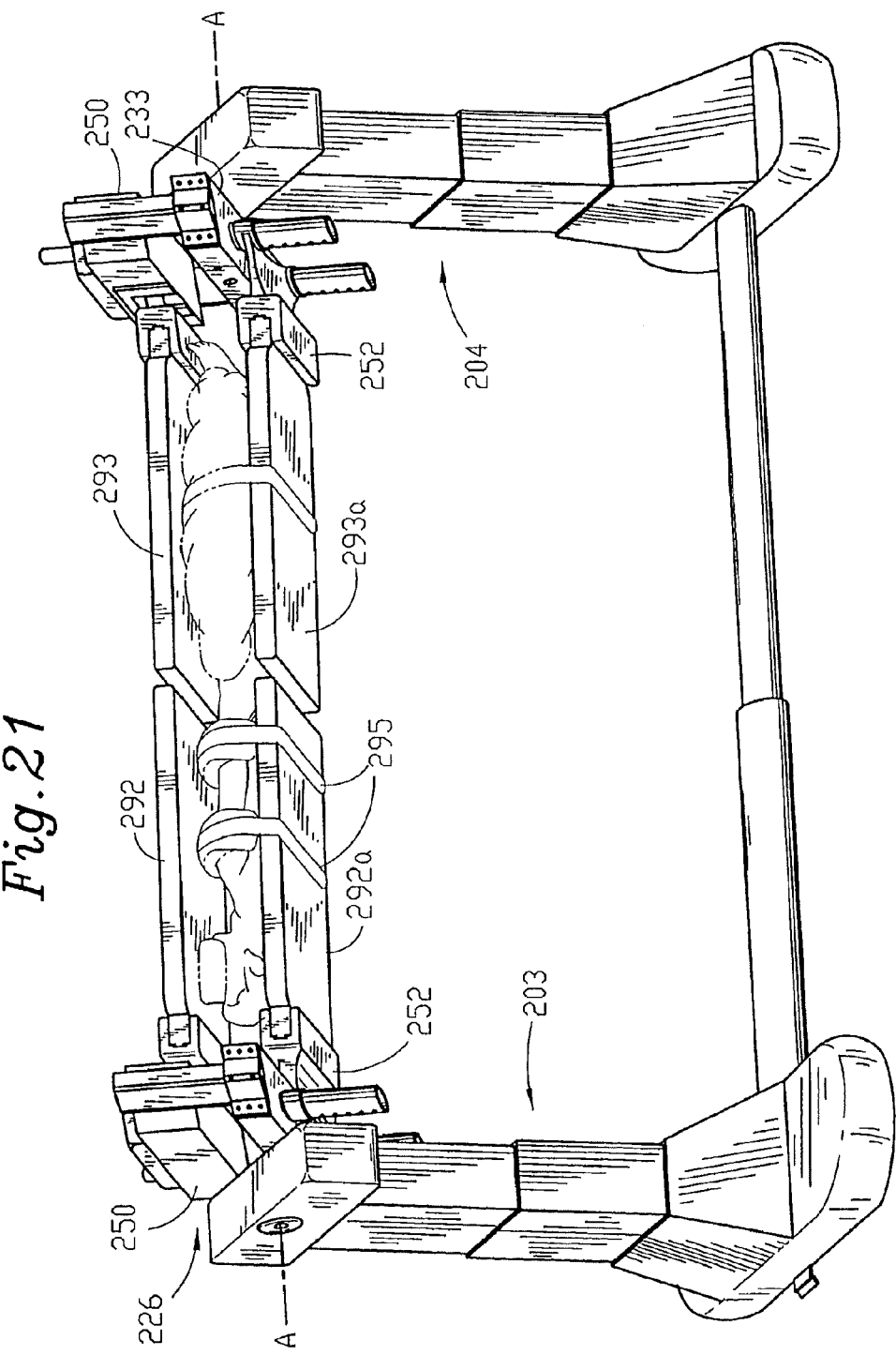
FIG. 21 is a side perspective view similar to FIG. 20, with the first set of patient support structures fully lowered to a patient-contacting position, and the structures and patient rotated approximately 30°.
Figure 22:
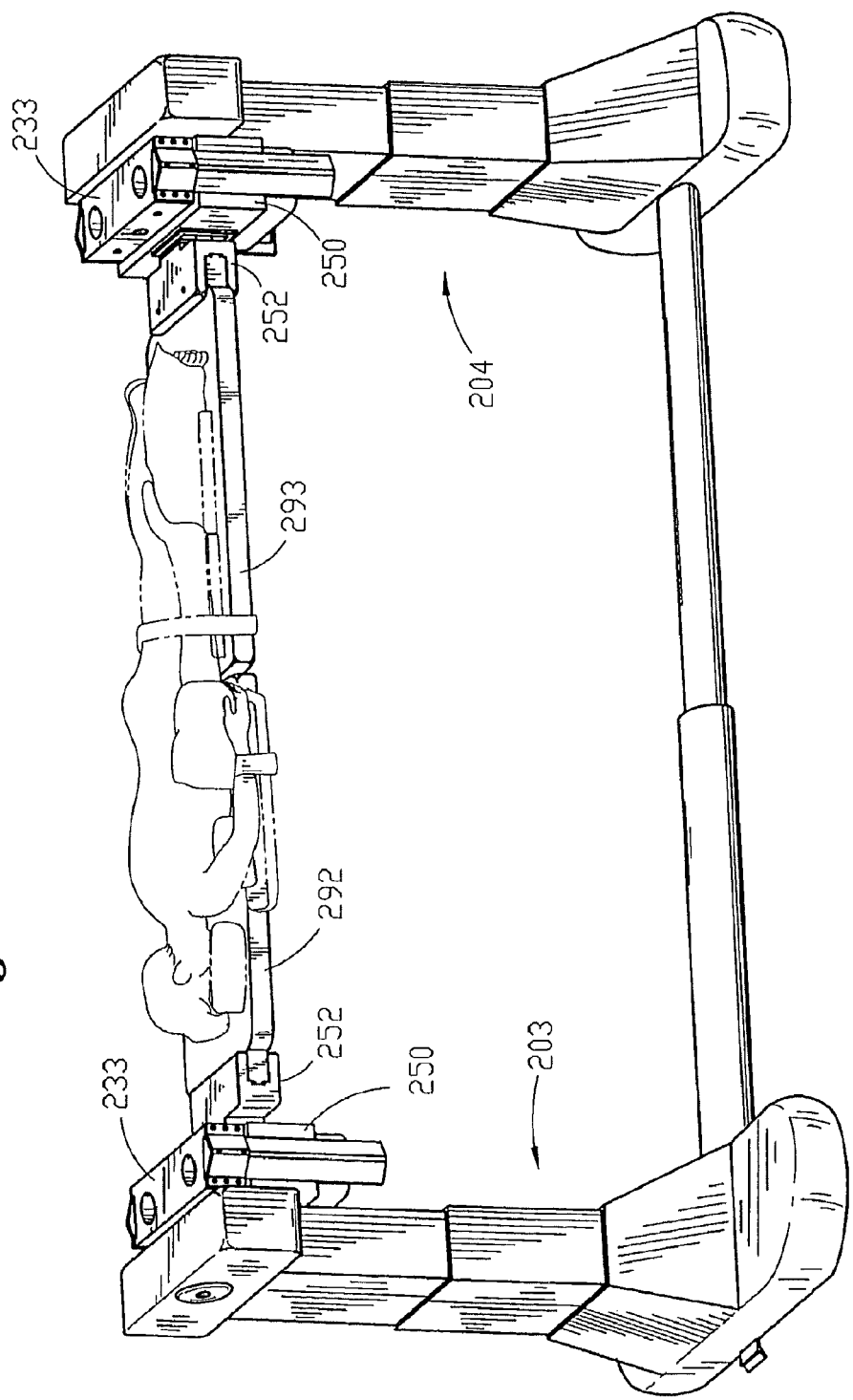
FIG. 22 is a side perspective view of the system following 180° rotation, with the patient in a prone position and the second set of patient support structures removed.

The rotation subassembly 226 is next actuated to rotate the blocks 233 along with the body boards 292*a* and 293*a* and the attached gear boxes 250 and attached body boards 292 and 293 with the patient in the generally supine position shown in FIG. 21 to the generally prone position shown in FIG. 22. The rotation subassembly 226 cooperates with the angulation subassembly 227, the support columns 203 and 204 and the separation subassembly 228 to enable rotation of the patient support structures 210 and 210*a* about a longitudinal axis, that is preselected according to the respective selected heights of the support columns 203 and 204 and the respective selected separation spacing of the patient supports 292 and 293 and 292*a* and 293*a* by the guide rails 281. As indicated by the arrows, the system 201 may be rotated 360° in either clockwise or counterclockwise direction.

Once the patient has been repositioned, the second patient support structure 210*a*, including the boards 292*a* and 293*a* and associated brackets 252 and riser posts 248 may be removed to provide full access to the surgical field. The linear guide rail subassemblies 228 may be actuated to raise the gear boxes 250 and connected body boards 292 and 293 up to a position adjacent the blocks 233.

As shown in FIG. 23, the angulation subassemblies 227 cooperate with the support columns 203 and 204 to permit independent adjustment of the height of the support columns, so that the body boards 292 and 293 may be set at an angle, with the patient's head above or below the feet. Cooperation of the angulation subassemblies 227 with the support columns 203 and 204 and with the telescoping crossbar 213 enables positioning of the patient with the head and torso horizontal in an upper plane and with the lower legs horizontal in a lower plane as shown in FIG. 26 and coordinated upward tipping of the patient with the head and torso and lower legs maintained in parallel angled planes as shown in FIG. 27.

It is to be understood that while certain forms of the present invention have been illustrated and described herein, it is not to be limited to the specific forms or arrangement of parts described and shown.

What is claimed is:

1. A surgical table comprising:
   A) a patient support comprising a first end, a second end opposite the first end, and a joint intermediate the first and second ends and about which the first and second ends articulate relative to each other;
   B) a first vertical support supporting a first displacement apparatus operably coupling the first vertical support to the first end of the patient support, the first vertical support comprising a first vertical elevator assembly that vertically extends and retracts the first vertical support, the first displacement apparatus comprising:
      a) a first rotation assembly operably coupled between the first vertical support and the first end of the patient support, the first rotation assembly configured to rotate the patient support relative to first vertical support and about an axis parallel to a longitudinal axis of the patient support; and
      b) a first angulation assembly operably coupled between the first vertical support and the first end of the patient support, the first angulation assembly configured to facilitate the first end articulating relative to second end about the joint; and
   C) a second vertical elevator assembly operably coupled between the first vertical support and the first end of the patient support, the second vertical elevator assembly vertically displacing the first angulation assembly relative to a top end of the first vertical support.

2. The surgical table of claim 1, wherein the first rotation assembly is located between the first angulation assembly and the first vertical support.

3. The surgical table of claim 1, wherein the first angulation assembly comprises:
   i) a first member operably coupled to the first vertical support via a first pivot; and
   ii) a second member operably coupled to the patient support near the first end, the second member configured to displace along a longitudinal length of the first member as the first and second ends articulate relative to each other about the joint.

4. The surgical table of claim 3, wherein the first rotation assembly is located between the first pivot and the first vertical support.

5. The surgical table of claim 4, wherein the first pivot includes a pivot axis that is transverse to the longitudinal axis of the patient support.

6. The surgical table of claim 2, wherein the first member comprises a lead screw and rotation of the lead screw causes the second member to displace along the longitudinal length of the first member.

7. The surgical table of claim 2, wherein the first displacement apparatus further comprises a first housing operably coupled to the first vertical support, the first pivot operably coupled to the first housing.

8. The surgical table of claim 7, wherein the rotation assembly operably couples the first housing and the first vertical support.

9. The surgical table of claim 7, wherein the first pivot comprises a first motor housing mount pivotally supported in the first housing.

10. The surgical table of claim 2, wherein the first pivot is located below the first pivot shaft.

11. The surgical table of claim 10, wherein the first pivot is suspended off the first pivot shaft.

12. The surgical table of claim 3, further comprising:
   D) a second vertical support supporting a second displacement apparatus operably coupling the second vertical support to the second end of the patient support, the second vertical support comprising a third vertical elevator assembly that vertically extends and retracts the second vertical support, the second displacement apparatus comprising:
      a) a second rotation assembly operably coupled between the second vertical support and the second end of the patient support, the second rotation assembly configured to rotate the patient support relative to second vertical support and about the axis parallel to the longitudinal axis of the patient support; and
      b) a second angulation assembly operably coupled between the second vertical support and the second end of the patient support, the second angulation assembly configured to facilitate the second end articulating relative to the first end about the joint, the second angulation assembly comprising a second pivot between the second vertical support and the second end of the patient support.

13. The surgical table of claim 12, further comprising a base extending between the first vertical support and the second vertical support, wherein the base is adjustable along its length.

14. The surgical table of claim 13, wherein the base is adjustable along its length via a telescopic configuration of at least a portion of the base.

15. The surgical table of claim 12, wherein at least one of the first vertical elevator assembly or third vertical elevator assembly comprises a telescopic configuration.

16. The surgical table of claim 12, wherein the second rotation assembly is located between the second angulation assembly and the second vertical support.

17. The surgical table of claim 16, wherein the second rotation assembly is located between the second pivot and the second vertical support.

18. The surgical table of claim 17, wherein the second pivot includes a pivot axis that is transverse to the longitudinal axis of the patient support.

19. The surgical table of claim 12, the first rotation assembly comprises a first pivot shaft and the second rotation assembly comprises a second pivot shaft, wherein the first pivot shaft and the second pivot shaft each comprises a pivot axis that is parallel to a longitudinal axis of the patient support.

20. The surgical table of claim 12, wherein the first pivot is located below the first pivot shaft, and the second pivot is located below the second pivot shaft.

21. The surgical table of claim 20, wherein the first pivot is suspended off the first pivot shaft, and the second pivot is suspended off the second pivot shaft.

22. The surgical table of claim 1, wherein the first angulation assembly is supported off of the second elevator assembly and configured to vertically displace along the second elevator assembly relative to the first vertical support.

23. The surgical table of claim 22, wherein the second elevator assembly comprises a vertical rail along which the first angulation assembly moves when vertically displacing along the second elevator assembly relative to the first vertical support.

24. The surgical table of claim 22, wherein the second elevator assembly facilitates the first angulation assembly spacing apart from the first rotation assembly.

* * * * *

UNITED STATES PATENT AND TRADEMARK OFFICE
CERTIFICATE OF CORRECTION

| | | |
|---|---|---|
| PATENT NO. | : 8,826,474 B2 | Page 1 of 1 |
| APPLICATION NO. | : 13/902525 | |
| DATED | : September 9, 2014 | |
| INVENTOR(S) | : Roger P. Jackson | |

It is certified that error appears in the above-identified patent and that said Letters Patent is hereby corrected as shown below:

On the Title page of the patent:

(63) "Continuation" should be --Continuation-in-part-- of application No. 13/317,012

Signed and Sealed this
Thirteenth Day of January, 2015

Michelle K. Lee
*Deputy Director of the United States Patent and Trademark Office*